(12) United States Patent     (10) Patent No.:    US 8,226,698 B2
Edelman et al.                                  (45) Date of Patent:      Jul. 24, 2012

(54) THERAPEUTIC CRANIAL WRAP FOR A CONTRAST THERAPY SYSTEM

(75) Inventors: Howard Edelman, San Francisco, CA (US); Elena Mednikoff, Burlingame, CA (US); Daqing Liu, San Mateo, CA (US)

(73) Assignee: VitalWear, Inc., South San Francisco, CA (US)

( * ) Notice: Subject to any disclaimer, the term of this patent is extended or adjusted under 35 U.S.C. 154(b) by 941 days.

(21) Appl. No.: 12/237,074

(22) Filed: Sep. 24, 2008
(Under 37 CFR 1.47)

(65) Prior Publication Data

US 2010/0030306 A1     Feb. 4, 2010

Related U.S. Application Data

(63) Continuation-in-part of application No. 10/267,247, filed on Oct. 8, 2002, now Pat. No. 7,211,104.

(51) Int. Cl.
*A61F 7/02* (2006.01)
(52) U.S. Cl. ........ 607/104; 607/108; 607/109; 607/112; 607/114
(58) Field of Classification Search .................. 607/104, 607/108–110, 112, 114
See application file for complete search history.

(56) References Cited

U.S. PATENT DOCUMENTS

| | | | |
|---|---|---|---|
| 26,663 A | 1/1860 | French | |
| 301,931 A | 7/1884 | Smith et al. | |
| 340,793 A | 4/1886 | Leonard | |
| 691,270 A | 1/1902 | Jones | |
| 787,920 A | 4/1905 | Hofmann | |
| 1,710,882 A | 2/1928 | Larson | |
| 1,907,709 A | 5/1931 | Barrow | |
| 2,726,658 A | 12/1955 | Chessey | |
| 2,911,974 A | 11/1959 | Sperce | |
| 3,090,045 A | 5/1963 | Hurst | |
| 3,548,819 A | 12/1970 | Davis et al. | |
| 3,612,059 A | 10/1971 | Ersec | |
| 3,683,902 A | 8/1972 | Artemenko et al. | |
| 3,696,814 A | 10/1972 | Umemoto | |
| 3,871,381 A | 3/1975 | Roslonski | |
| 3,901,225 A | 8/1975 | Sconce | |
| 3,995,621 A | 12/1976 | Fletcher et al. | |
| 4,061,898 A | 12/1977 | Murray et al. | |

(Continued)

FOREIGN PATENT DOCUMENTS

DE           3410413 A1     10/1985

(Continued)

*Primary Examiner* — Roy Gibson
(74) *Attorney, Agent, or Firm* — Kang S. Lim

(57) ABSTRACT

The present invention relates to a therapeutic cranial wrap for use with a thermal contrast therapy systems and methods for providing a temperature regulated fluid. The cranial wrap includes an active thermal exchange bladder and an active compression bladder, adapted to fit the cranial therapy site. The thermal exchange bladder may be coupled to the thermal contrast therapy system. The compression bladder may compress the therapy site. In some embodiments, the compressive bladder may be integrated into the thermal exchange bladder, or may be omitted. The cranial wrap also includes a contoured shell, known as a hood shaped therapy pad, which is adapted to snugly fit the cranial therapy site and provide neck support. Adjustable straps, including at least one strap that circumvents the cranium, secure the cranial wrap in a fitted position adjacent the therapy site. The cranial wrap couples to the thermal contrast therapy system which includes a hot and cold fluid reservoir, a mixing valve, and a fluid pump.

25 Claims, 21 Drawing Sheets

U.S. PATENT DOCUMENTS

| | | | |
|---|---|---|---|
| 4,138,743 A * | 2/1979 | Elkins et al. | 2/171.2 |
| 4,149,541 A | 4/1979 | Gammons et al. | |
| 4,196,772 A | 4/1980 | Adamski et al. | |
| 4,338,944 A | 7/1982 | Arkans | |
| 4,382,446 A * | 5/1983 | Truelock et al. | 607/110 |
| 4,459,471 A | 7/1984 | Hulett et al. | |
| 4,551,858 A | 11/1985 | Pasternack | |
| 4,669,476 A | 6/1987 | Gordon et al. | |
| 4,691,762 A | 9/1987 | Elkins et al. | |
| 4,744,106 A | 5/1988 | Wang | |
| 4,781,193 A * | 11/1988 | Pagden | 607/104 |
| 4,844,072 A | 7/1989 | French et al. | |
| 4,846,176 A | 7/1989 | Golden | |
| 5,072,875 A | 12/1991 | Zacoi | |
| 5,080,089 A | 1/1992 | Mason et al. | |
| 5,143,064 A | 9/1992 | Cochran | |
| D331,115 S | 11/1992 | Stout | |
| D333,350 S | 2/1993 | Redira, Jr. | |
| 5,230,335 A | 7/1993 | Johnson, Jr. et al. | |
| D344,343 S | 2/1994 | McNew | |
| 5,314,455 A | 5/1994 | Johnson, Jr. et al. | |
| 5,324,318 A | 6/1994 | Smith | |
| 5,324,319 A | 6/1994 | Mason et al. | |
| 5,330,519 A | 7/1994 | Mason et al. | |
| 5,342,411 A | 8/1994 | Maxted et al. | |
| 5,344,436 A | 9/1994 | Fontenot et al. | |
| 5,372,608 A | 12/1994 | Johnson | |
| 5,383,919 A | 1/1995 | Kelly et al. | |
| D358,216 S | 5/1995 | Dye | |
| 5,411,541 A | 5/1995 | Bell et al. | |
| 5,417,720 A | 5/1995 | Mason | |
| 5,433,083 A | 7/1995 | Kuramarohit | |
| 5,441,533 A | 8/1995 | Johnson et al. | |
| 5,449,379 A | 9/1995 | Hadtke | |
| 5,456,701 A | 10/1995 | Stout | |
| 5,466,250 A | 11/1995 | Johnson, Jr. et al. | |
| 5,466,251 A | 11/1995 | Brunson et al. | |
| 5,469,579 A | 11/1995 | Tremblay et al. | |
| 5,476,489 A | 12/1995 | Koewler | |
| 5,486,207 A | 1/1996 | Mahawili | |
| 5,507,792 A | 4/1996 | Mason et al. | |
| 5,555,579 A | 9/1996 | Wu | |
| 5,562,604 A | 10/1996 | Yablon et al. | |
| 5,603,728 A | 2/1997 | Pachys | |
| 5,609,619 A | 3/1997 | Pompei | |
| 5,662,695 A | 9/1997 | Mason et al. | |
| 5,715,533 A | 2/1998 | Stein | |
| D393,719 S | 4/1998 | Nichols | |
| 5,894,615 A | 4/1999 | Alexander | |
| 5,940,880 A | 8/1999 | Phillips | |
| 5,968,072 A | 10/1999 | Hite et al. | |
| 6,312,453 B1 | 11/2001 | Stefanile et al. | |
| 6,551,347 B1 * | 4/2003 | Elkins | 607/104 |
| 6,581,400 B2 | 6/2003 | Augustine et al. | |
| 6,962,600 B2 | 11/2005 | Lennox et al. | |
| 6,986,783 B2 | 1/2006 | Gunn et al. | |
| 7,008,445 B2 | 3/2006 | Lennox | |
| 7,211,104 B2 | 5/2007 | Edelman | |
| 2001/0039439 A1 | 11/2001 | Elkins et al. | |
| 2002/0161419 A1 | 10/2002 | Carson et al. | |

FOREIGN PATENT DOCUMENTS

GB  2 175 496 A  12/1986

* cited by examiner

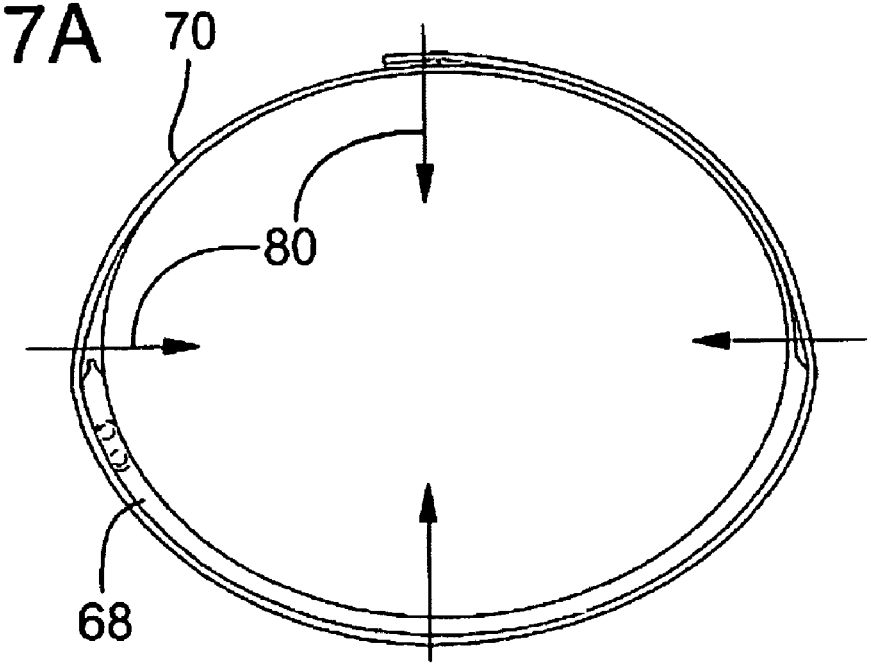

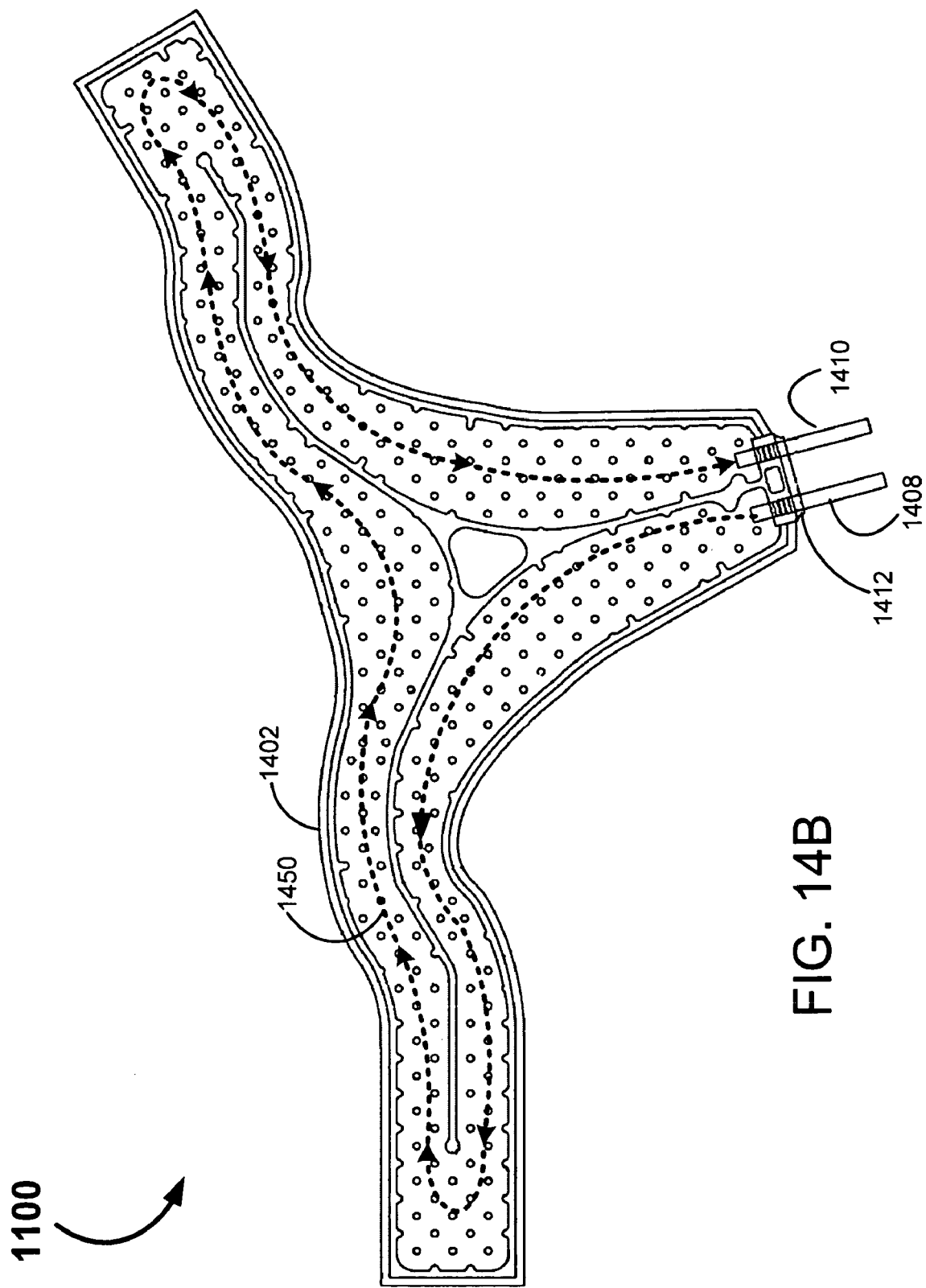

THERAPEUTIC CRANIAL WRAP FOR A CONTRAST THERAPY SYSTEM

CROSS REFERENCE TO RELATED APPLICATIONS

This is a continuation-in-part of U.S. application Ser. No. 10/267,247 filed on Oct. 8, 2002, entitled "Contrast Therapy System and Method", now U.S. Pat. No. 7,211,104, which is hereby fully incorporated by reference.

BACKGROUND OF THE INVENTION

The present invention relates to a cranial wrap, and more particularly, to a cranial wrap which incorporate bladders, and which are adapted for use in a thermal or contrast therapy system, or medical thermal therapy system. The bladder element of the present invention enables the user to obtain a tightly controlled and consistent temperature or contrast therapy, along with support, pressure and/or compression therapy.

Head injuries may be extremely painful and are prone to excessive swelling. Likewise, neck injuries are often greatly debilitating, as well as painful. Contrast therapy has been shown to be an effective method for treatment of injuries such as those that often occur in the head and neck regions. Healing time for such injuries may be reduced, and the pain associated with the injury may likewise be minimized with proper temperature therapy.

In addition to treating head and neck injuries, temperature therapy has been known to be an effective treatment for a host of other head pains, including headaches. Migraine headaches, tension headaches and cluster headaches are three popular primary varieties of headaches. Tension headaches and cluster headaches focus along the frontal lobe or above the eyes. Migraine pain may be centered more in the occipital lobe or the back of the head.

Migraines affect roughly 12-20% of all individuals at some point in their lives. Unlike a traditional headache, the Migraine disease has many symptoms, including nausea, vomiting, auras (light spots), sensitivity to light and sound, numbness, difficulty in speech, and severe semi-hemispherical head pain. One Migraine attack alone can last for eight hours, several days, or even weeks.

Moreover, a migraine may induce a host of serious physical conditions such as strokes, aneurysms, permanent visual loss, severe dental problems, coma and even death. According to the New England Journal of Medicine, a migraine can sometimes lead to ischemic stroke and stroke can sometimes be aggravated by or associated with the development of migraine. Twenty-seven percent of all strokes suffered by persons under the age of 45 are caused by Migraine. Stroke is the third leading cause of death in this country. In addition, twenty-five percent of all incidents of cerebral infarction were associated with Migraines, according to the Mayo clinic.

Not only can the Migraine disease be life threatening, but it can have a devastating and disruptive effect on normal living. Migraine sufferers experience not only excruciating pain, but social ostracism, job loss, disruption to personal relationships, and prejudices in the workplace.

A recent study showed that the loss of labor time and lost productivity of Migraine sufferers may exact a significant toll on U.S. business. According to a position paper signed by the American Academy of Pain Medicine, et. al., 150 million work days per year, equivalent to 1,200 million work hours, are lost each year to head pain. The corresponding annual cost to industry and the health care system due to Migraine amounts to $5 to $17 billion.

The root cause of migraines has not been readily identified, thus it is common for physicians to prescribe potentially addictive and powerful pain relievers, such as Vicodin®, to individuals that experience frequent migraine headaches.

It is known, however, that the pain resulting from a migraine is caused by vasodilatation in the cranial blood vessels (expansion of the blood vessels). Traditional headache pain is caused by vasoconstriction (narrowing of the blood vessels). During a migraine, inflammation of the tissue surrounding the brain, i.e., neurogenic inflammation, exacerbates the pain. Therefore, medicine often prescribed to treat a headache, such as beta-blockers, dilate the blood vessels and therefore can make a Migraine even worse.

It has been found that temperature regulation around the neck and cranium may be as, if not more, effective in migraine treatment as traditional pharmaceuticals.

Numerous thermal therapy devices that apply external treatments to the body are known in the art. Thermal or contrast therapy devices deliver or remove heat to a given therapy area for an effective amount of time in order to achieve a desired therapeutic result. Contrast therapy devices are used to reduce swelling or to encourage healing after swelling has receded. They are also used to soothe muscle and joint pain through the application of heat and compression therapy. Application of heat or cold may be used to heal and rehabilitate injuries to bone, muscle, ligaments, tendons and skin. Cold therapy may be used to reduce swelling, decrease pain, and promote healing of injured tissue. Heat therapy can be used to relax joint tissue, such as ligaments and tendons, to increase range of motion. Thermal therapy can also be used after surgery to reduce pain and swelling and promote healing.

Lastly, dependent upon pain source, it may be desirous to apply heat alone, cold alone or some combination of the two. For example, migraine pain resulting from vasodilatation may be best treated with a cold treatment. Whereas a tension headache, which includes vasoconstriction, may be best treated by a hot therapy. Lastly, a neck injury, such as a pulled ligament, may be best treated with a contrast therapy. Currently, there is a lack of systems capable of providing such a range or highly controlled temperature treatments to the cranium and neck.

The potential effectiveness of a hot or cold treatment increases as the level of control for the treatment increases. In particular, the effectiveness depends on the ability to control the temperature of the treatment. If cold treatments are too cold, they may cause skin and tissue damage. Similarly, if hot treatments are too hot, they may burn or otherwise damage the recipient. The effectiveness of a therapy also is dependent on the ease in which the therapy may be applied. If it is difficult for a therapy recipient to self apply a therapy, the opportunity to receive therapy may be diminished. Furthermore, if therapies are complicated and/or uncomfortable, a therapy recipient is less likely to undergo the therapy, although it may be beneficial.

Due to the shape of the head, it is often cumbersome to apply external temperature regulators to the head and neck for a prolonged period of time in a comfortable fashion. Cold compresses, the most common form of cranial temperature regulation, are atrocious at maintaining constant temperature and are burdensome to apply, as they often leak and typically require the user to lie down or manually hold the compress to the desired area. Likewise, compresses are typically applied to the forehead, or other localized area of the cranium, and as such, are incapable of targeting a range of therapeutic points.

It is therefore apparent that an urgent need exists for an improved cranial wrap that is capable of contrast and stable temperature therapy. This cranial wrap would be able to provide neck support with the addition of a thermal therapy that may be very well regulated and applied to the entire cranium and neck regions.

SUMMARY OF THE INVENTION

To achieve the foregoing and in accordance with the present invention, a Cranial Wrap System for use with a thermal contrast therapy systems and methods for providing a temperature regulated fluid are provided. Such systems are useful for providing effective neck support with integrated contrast thermal therapy.

The cranial wrap system includes an active thermal exchange bladder and an active compression bladder, adapted to fit the cranial therapy site. The thermal exchange bladder may be coupled to the thermal contrast therapy system, and may receive therapy fluid to tightly regulate the temperature of the therapy site. The compression bladder may compress the therapy site. In some embodiments the compressive bladder may be integrated into the thermal exchange bladder. In other embodiments the compression bladder may be omitted.

The cranial wrap system may also include a contoured shell, known as a hood shaped therapy pad, which is adapted to snugly fit the cranial therapy site. The hood shaped therapy pad may further provide neck support. Adjustable straps may secure the therapeutic cranial wrap system in a fitted position adjacent the cranial therapy site and compress the therapeutic cranial wrap system against the cranial therapy site. The strapping system includes at least one strap that circumvents the cranium.

The cranial wrap system may couple to the thermal contrast therapy system which includes a hot fluid reservoir, a cold fluid reservoir, a mixing valve, and a fluid pump for delivering the therapy fluid to the thermal exchange bladder.

A thermal bladder envelope receives the thermal exchange bladder and a compression bladder envelope that receives the compression bladder. These envelopes may be integrated within the hood shaped therapy pad in some embodiments. The therapy pad may also include at least one cushion layer, adapted to provide comfort and adapted to aid in securing the therapeutic cranial wrap system in the fitted position adjacent the cranial therapy site.

The pump may cause constant pressure, or dynamic pressure, within the compression bladder. Constant pressure produces steady compression on the therapy site, whereas dynamic pressure produces pulsating compression on the therapy site.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIG. 7A is a cross-sectional view of the therapy pad of FIG. 7 wrapped around the therapy recipient;

FIG. 14B is an illustration of the fluid path in the thermal bladder of the cranial wrap in accordance with an embodiment of the present invention;

DETAILED DESCRIPTION OF THE INVENTION

Figure 1:
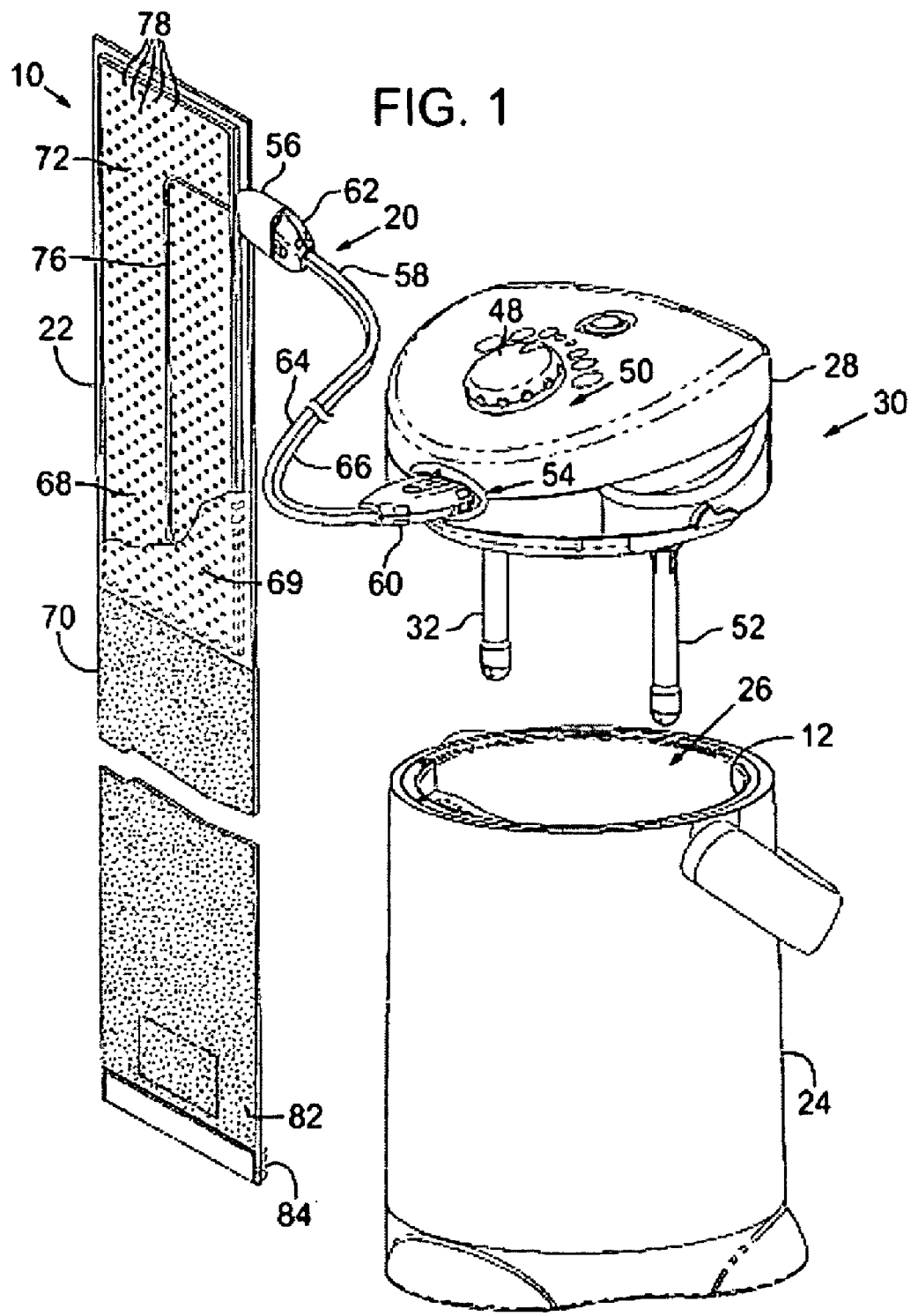
FIG. 1 is an isometric view of one embodiment of the contrast therapy system in accordance with the present invention.

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

The present invention relates to therapeutic cranial wrap system including thermal contrast therapy systems and a method of providing contrast therapy. To facilitate discussion, FIGS. 1 through 8 show various views of the present contrast therapy system. FIGS. 9A to 11 provide illustrations of the cranial wrap being worn by a therapy recipient. FIGS. 12 through 14D show various views of the present cranial wrap and contrast therapy bladder utilized by the cranial wrap. FIG. 15 provides an flow diagram of a method for providing contrast therapy to a therapy recipient.

Although useful for applying any combination of heat, cold, compression and neck support to a recipient for virtually any reason, the Therapeutic Cranial Wrap 920 including Thermal Contrast Therapy Systems 10 described below demonstrates particular utility for treating sore, strained, arthritic, injured, post operable, heavily exercised, and/or otherwise taxed neck and head regions. Additionally, the Therapeutic Cranial Wrap Therapeutic Cranial Wrap 920 may be of particularly beneficial use for those who suffer from frequent migraine and other headaches.

The contrast therapy system is described below in the context of providing "therapy" to a recipient, however, it should be understood that the Therapeutic Cranial Wrap 920 including Thermal Contrast Therapy Systems 10 are equally well suited for providing any combination of heat, cold, compression and support for what may be considered non-therapeutic purposes.

As described herein, the Contrast Therapy System 10 is capable of imparting a desired therapy temperature to a Therapy Pad 22 or in the present invention a Hood Shaped Therapy Pad 922, which may be applied to a therapy recipient. The system is capable of shifting the therapy temperature between hot and cold temperatures very quickly, which has proven to be beneficial. The precise temperature may be set at any temperature between controlled maximum and minimum temperatures. Furthermore, the contrast therapy system may be designed as a relatively small portable unit, as shown at 30 of FIG. 1, which is both easy and inexpensive to operate. The Portable Unit 30 includes a Container 24 and a Lid Unit 28. The Lid Unit 28 includes a Dial 48 and Indicia 50 to aid in the temperature control of the contrast therapy. The Container 24 may include a Cold Reservoir 12 and an Open End 26 that the Lid Unit 28 may fit into.

As described herein, the Therapeutic Cranial Wrap 920 is capable of imparting neck support to a therapy recipient, and provides a medium for the Contrast Therapy System 10. The Therapeutic Cranial Wrap 920 may include a Hood Shaped Therapy Pad 922, a Neck Compress 924, and a Cranial Contrast Therapy Bladder 1100. Additional features may be incorporated into the Therapeutic Cranial Wrap 920 as addressed below.

The Cranial Contrast Therapy Bladder 1100 may be coupled to the contrast therapy system Portable Unit 30 through a Fluidic Coupling Assembly 20. The Hood Shaped Therapy Pad 922, as seen in FIGS. 9A to 13 includes the integrated Cranial Contrast Therapy Bladder 1100, seen in FIG. 13. The Hood Shaped Therapy Pad 922 may have a First Face 1426 comprised of a mesh, or other efficient thermal exchange medium, to ensure rapid transference of temperature from the Hood Shaped Therapy Pad 922 to the therapy recipient. Additionally, the Hood Shaped Therapy Pad 922 may utilize adjustable elastic straps for securing the Hood Shaped Therapy Pad 922 to the therapy site. Hook material pads on the adjustable elastic straps may releasably engage complimentary loop material on the adjustable elastic strap surface thereby allowing for adjustable tension of the adjustable elastic straps.

The system is also capable of applying compressive force to a therapy recipient through the Hood Shaped Therapy Pad 922, thus increasing the effectiveness of treatments and further providing internal support of the neck.

The following description of some embodiments of the present invention will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Fluid Circuit

Figure 2:
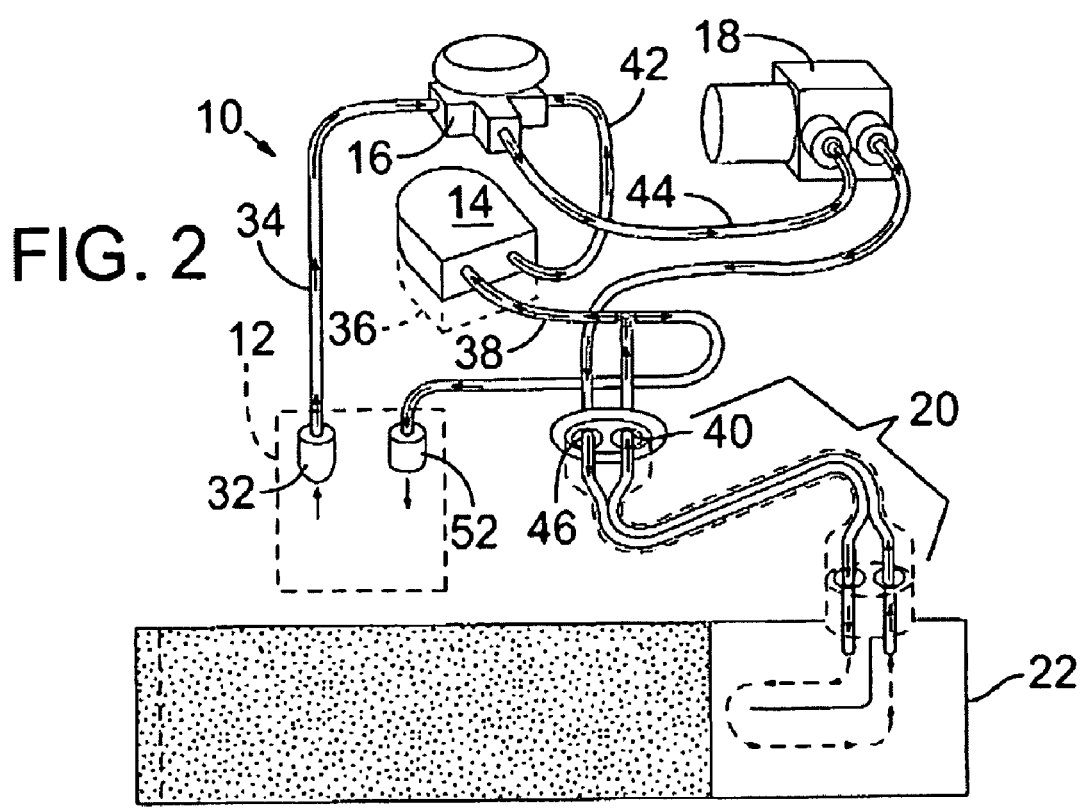
FIG. 2 is a schematic view of a fluid circuit for administering contrast therapy in accordance with an embodiment of the present invention.
Figure 3:
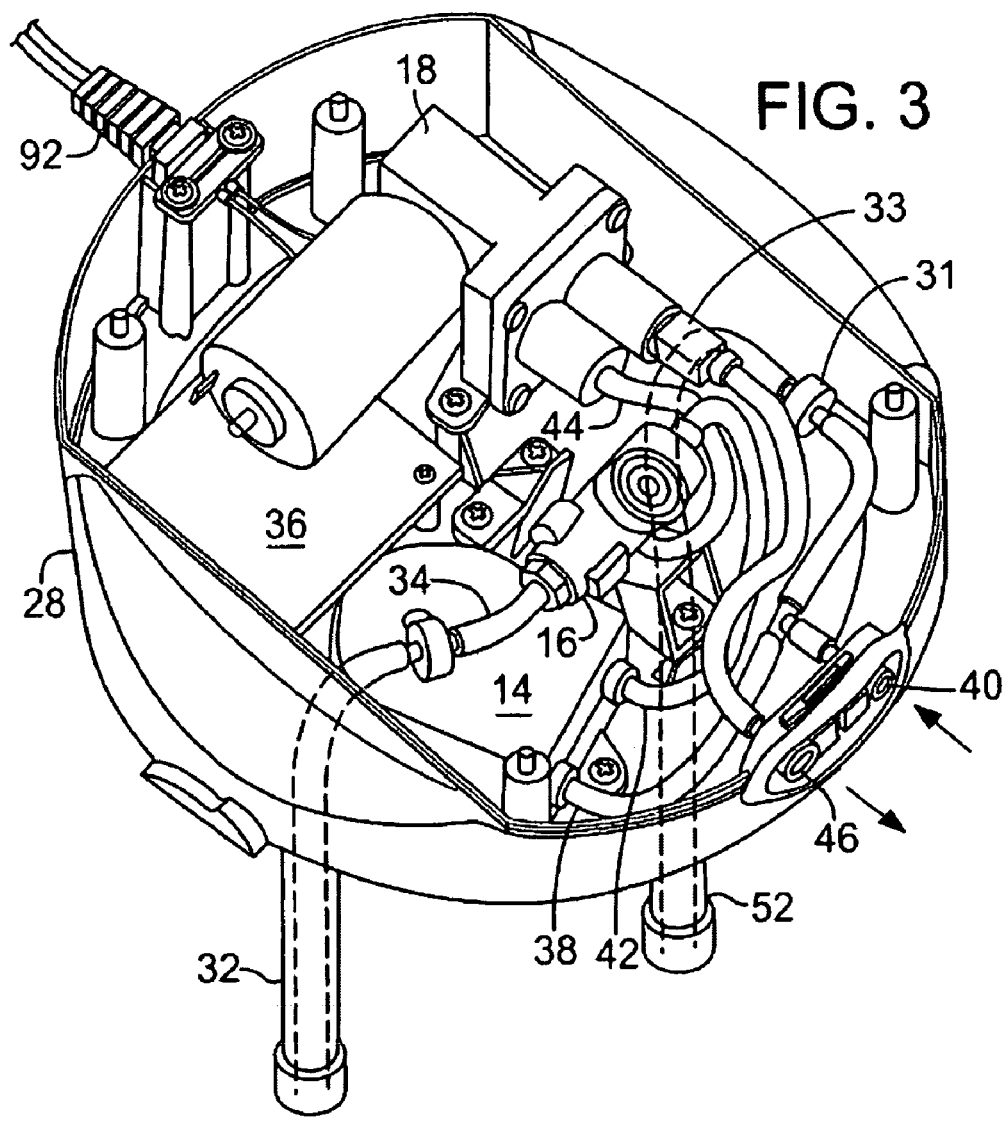
FIG. 3 is an isometric view of the fluid circuit of FIG. 2 housed within the lid portion of the contrast therapy system of FIG. 1.

FIG. 2 schematically shows a fluid circuit of the Therapeutic Cranial Wrap 920 including a Contrast Therapy System 10, and FIG. 3 shows such a circuit housed by the Lid Unit 28 of a Portable Control Unit 30. As illustrated in FIGS. 2 and 3, the Contrast Therapy System 10 includes a Cold Reservoir 12, Hot Reservoir 14, Mixing Valve 16, Pump 18, Fluidic Coupling Assembly 20, and Therapy Pad 22 which may be the Hood Shaped Therapy Pad 922. As described in detail below, the Contrast Therapy System 10 is designed to control the temperature of a therapy fluid that circulates through the Therapy Pad 22, which includes the present Hood Shaped Therapy Pad 922. Mixing Valve 16 selectively combines fluid received from the cold and hot reservoirs and passes the combined fluid to the Therapy Pad 22 as a therapy fluid. The Mixing Valve 16 may control the temperature of the therapy fluid, changing between hot and cold temperatures in a short period of time.

Cold Reservoir 12 is designed to hold a relatively cold fluid, which may be passed to the Mixing Valve 16 and eventually to the Therapy Pad 22. As shown in FIG. 1, Cold Reservoir 12 may include the Container 24 with an Open End 26 suitable for receiving the Lid Unit 28. The Container 24 and the Lid Unit 28 may be components of the Portable Control Unit 30. The Cold Reservoir 12 may be dimensioned to hold virtually any volume of fluid, and is shown as a 4.2 Liter receptacle. Of course, smaller Cold Reservoirs 12 may be used, for example, when increased portability is desired, and larger Cold Reservoirs 12 may be used when, for example, increased capacity is desired.

The temperature of the Cold Reservoir 12 may be controlled by various mechanisms. In some embodiments, the Cold Reservoir 12 is adapted to receive ice that may melt in the Cold Reservoir 12, and thus decrease the temperature of the fluid in the Cold Reservoir 12. As shown in FIG. 1, Container 24 has a large Open End 26 that is suitable for easily receiving ice. In some embodiments, the Cold Reservoir 12 may include a cooler for cooling the fluid held in the Cold Reservoir 12. Such a cooler may include a compressor and a refrigerant, or similar cooling mechanism. It is within the scope of the invention, however, to use virtually any other suitable method for cooling the fluid held in Cold Reservoir 12. The Cold Reservoir 12 may include insulation to limit heat transfer between the fluid held by the Cold Reservoir 12 and the external environment.

The minimum temperature of the fluid in Cold Reservoir 12 is usually limited to approximately 32 to 45 degrees Fahrenheit, although such a limitation is not necessary. In particular, it has been found that a temperature of about 32 to 45 degrees Fahrenheit is an appropriate minimum temperature. Although water is usually used as the fluid, it is within the scope of the invention to use other suitable fluids. Such fluids may be selected for particular applications based on their specific heat, viscosity, freezing point, etc.

The Contrast Therapy System 10 may include an Intake 32 for drawing fluid from the Cold Reservoir 12. The drawn fluid may pass through a Fluid Path 34 between Cold Reservoir 12 and Mixing Valve 16, as is schematically shown in FIG. 1. Fluid Path 34, as well as other Fluid Paths described herein, may utilize ⅛ inch flexible tubing, or may alternatively implement another suitable fluid transport mechanism. For example, some or all of the Fluid Paths 34 may alternatively be defined by inflexible fluid conduits. The Fluid Path 34, or other fluid channels such as Intake 32, may include filters, flow restrictors, and/or check valves. Filters may help prevent flow blockages resulting from jammed ice or other substances, and check valves may be used to prevent backflow in the system. The rate of fluid flow may be at least partially controlled by flow restrictors.

Hot Reservoir 14 is designed to hold a relatively hot fluid, which may be passed to the Mixing Valve 16 and eventually to the Therapy Pad 22. Fluid in the Hot Reservoir 14 may be heated by a Heater 36, which may be positioned adjacent the Hot Reservoir 14, or may be incorporated into the Hot Reservoir 14. The Hot Reservoir 14 may be dimensioned to hold virtually any volume of fluid, and is shown dimensioned to hold a volume of approximately 20 to 30 cubic centimeters. It should be understood that the Hot Reservoir 14 may be smaller or larger, depending on the desired use and the other components of the contrast therapy system. Additionally, the Hot Reservoir 14 may be insulated to prevent heat loss from the Hot Reservoir 14 fluid to the external environment.

Heater 36 may be configured so as to achieve a suitable balance of power consumption and heat generation. It has been found that a heater of approximately 280 Watts is appropriate for heating a volume of approximately 20 to 30 cubic centimeters under normal conditions. It should be understood that more powerful and less powerful Heaters 36 may be used. Similarly, more than one heater or type of heater may be used.

The flow rate of fluid through the Hot Reservoir 14 may correspond to the temperature of treatment being applied, with greater flow rates occurring during hotter treatments. During some hot treatments, Heater 36 may have limited time to increase the temperature of the fluid because the fluid quickly passes through the Hot Reservoir 14, and thus, the heater should be powered so as to increase the temperature a desired amount within that constrained timeframe. However, the Heater 36 does not need to completely heat the fluid from a minimum temperature to a maximum temperature in such a timeframe, although it is within the scope of the invention to do so. The Hot Reservoir 14 receives fluid from the Therapy Pad 22, and when a hot treatment is being applied, the return fluid may already be partially heated, decreasing the magnitude of heating required from Heater 36. Thus, the net temperature of the fluid may incrementally increase as it repeatedly circulates through the Hot Reservoir 14. Nevertheless, a more powerful heater may increase the rate fluid increases temperature in the Hot Reservoir 14 and/or the maximum temperature of the fluid, thus decreasing the time required to change from a cold treatment to a hot treatment. The maximum temperature of the fluid in Hot Reservoir 14 is usually limited to approximately 100 to 110 degrees Fahrenheit, although such a limitation is not required. In particular, it has been found that a temperature of about 105 degrees Fahrenheit is appropriate.

As illustrated in FIGS. 2 and 3, Hot Reservoir 14 receives fluid via a Fluid Path 38 coming from a Bulkhead Input 40. As described below, Bulkhead Input 40 receives fluid returning from the Therapy Pad 22. The returning fluid may be directed so that fluid may go to at least one of the Hot Reservoir 14, via Fluid Path 38, and the Cold Reservoir 12, via a Return 42. In some embodiments, the Hot Reservoir 14 may be housed within Lid Unit 28, which may be securely fit to Open End 26 of Container 24. Heater 36 may be controlled by an internal control system, external control system, or no control system whatsoever. If present, a control system may regulate the maximum temperature of fluid in the Hot Reservoir 14, for example. Such a control system may also be designed to maximize heating efficiency to limit energy requirements. Contrast Therapy System 10 may include a Power Supply, such as 92 of FIG. 3, for providing power to various components of the system, such as a heater, cooler, pump, thermostat, display, etc. In some embodiments, the power supply may provide alternating current, while in other embodiments, the power supply may provide direct current. Some embodiments may be configured to operate with either AC or DC power. For example, the contrast therapy system may include a DC heater and pump designed to draw power from either a battery or an electrical outlet via an AC/DC converter. Batteries used to power the contrast therapy system may be externally connected to the system, and/or housed within the system. The contrast therapy system may be powered from alternative power sources as well.

II. Mixing Valve

The Contrast Therapy System 10 includes the Mixing Valve 16 for receiving a selected ratio of the hot and cold fluids from the Hot Reservoir 14 and Cold Reservoir 12. The Mixing Valve 16 is operable to deliver a therapy fluid with a therapy temperature that is determined by the selected ratio. In other words, Mixing Valve 16 may adjustably control the amount of hot fluid from the Hot Reservoir 14 and the amount of cold fluid from the Cold Reservoir 12 that mix together. The ratio may be 100% hot fluid from the Hot Reservoir 14, in which case the resulting therapy fluid would have a therapy temperature substantially equal to the temperature of fluid leaving the Hot Reservoir 14 (maximum temperature). The ratio may alternatively be 100% cold fluid from the Cold Reservoir 12, in which case the resulting therapy fluid would have a therapy temperature substantially equal to the temperature of fluid leaving the Cold Reservoir 12 (minimum temperature). Any temperature in between the maximum and minimum temperature may be achieved by adjusting the ratio.

The mixing valve is linked to the Cold Reservoir 12 and the Hot Reservoir 14 by respective Fluid Paths 34 and 42. In some embodiments, one or both of Fluid Paths 34 and 42 may include a pump, although no pump is required. The Mixing Valve 16 outputs therapy fluid to a Fluid Path 44 that leads to the Bulkhead Output 46, and eventually to the Therapy Pad 22. A Pump 18 may be included between the Mixing Valve 16 and the Therapy Pad 22, as shown in FIGS. 2 and 3 and described below. As with the other Fluid Paths of the contrast therapy system, these Fluid Paths may include flow restrictors, check valves, filters, over-pressure switches, and/or other components. For example, Check Valve 31 and Over Pressure Switch 33 are illustrated in FIG. 3. The flow paths may include flexible rubber tubing that is approximately ⅛ inch in diameter.

As shown in FIG. 1, the Mixing Valve 16 may be controlled by a Dial 48 that adjusts the ratio of hot and cold fluids delivered from the mixing valve. The Dial 48 may be associated with Indicia 50 that indicate a relative magnitude of a desired therapy temperature. For example, Indicia 50 may include a series of icons representing relative temperatures. A large red dot may represent the hottest therapy temperature, with red dots decreasing in size representing decreasing temperatures. Similarly, a large blue dot may represent the coldest therapy temperature, with blue dots decreasing in size representing increasing temperatures. The Dial 48 positioned to point to the large red dot may correspond to a mixing valve position that yields a ratio of 100% hot fluid. As the Dial 48 is turned through the progressively smaller red dots, and then through the progressively larger blue dots, the ratio may yield a therapy fluid with a continually increasing percentage of cold fluid.

In some embodiments, the Contrast Therapy System 10 may include a thermostat that automatically selects the ratio of hot and cold fluids delivered from the Mixing Valve 16. For example, the thermostat may be designed to receive manual input of a desired therapy temperature, and adjust the mixing valve to yield a therapy fluid with that temperature. Accordingly, the thermostat may include a temperature measuring device (not shown), such as a thermistor, thermometer, thermocouple, etc. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of hot and cold fluids delivered from the mixing valve. For example, the thermostat may be programmed to provide alternating hot therapies that last for five minutes at 105 degrees Fahrenheit and cold therapies that last for 5 minutes at 40 degrees Fahrenheit. It should be understood that the thermostat may be programmed for therapies of different durations and/or temperatures.

As shown in FIGS. 2 and 3, the Contrast Therapy System 10 may include a Pump 18 for circulating fluid through the system. As illustrated, the Pump 18 interposes the Mixing Valve 16 and the Bulkhead Output 46, although the Pump 18 may be positioned elsewhere. Similarly, more than one pump may be utilized. As is shown, the Pump 18 may be integrated into the Lid Unit 24 of the Portable Control Unit 30. The Pump 18 may be powered according to the desired application, and a 4 Watt pump capable of pumping 300 cubic centimeters of fluid per minute has been found to be suitable. The Pump 18 may be a reciprocating pump, a rotary pump, or virtually any other suitable pump.

In some embodiments, the Pump 18 may be configured to pulse the therapy fluid through the Therapy Pad 22, or in the present instance the Thermal Exchange Layer 901. Such a pulsing action may be translated into a therapeutic massage via the Therapy Pad 22. As the pulsing fluid circulates through the Therapy Pad 22, the Therapy Pad 22 may vibrate. Pumps designed to pulse fluid may be further enabled to adjust the relative magnitude of the pulsing to correspond to different intensities of therapeutic massages. The relative intensity may be automatically, or manually, coordinated to correspond to a particular temperature of treatment. For example, a vigorous massage may be applied during a hot treatment while a milder massage is applied during a subsequent cold treatment.

III. Fluidic Coupling Assembly

Figure 4:
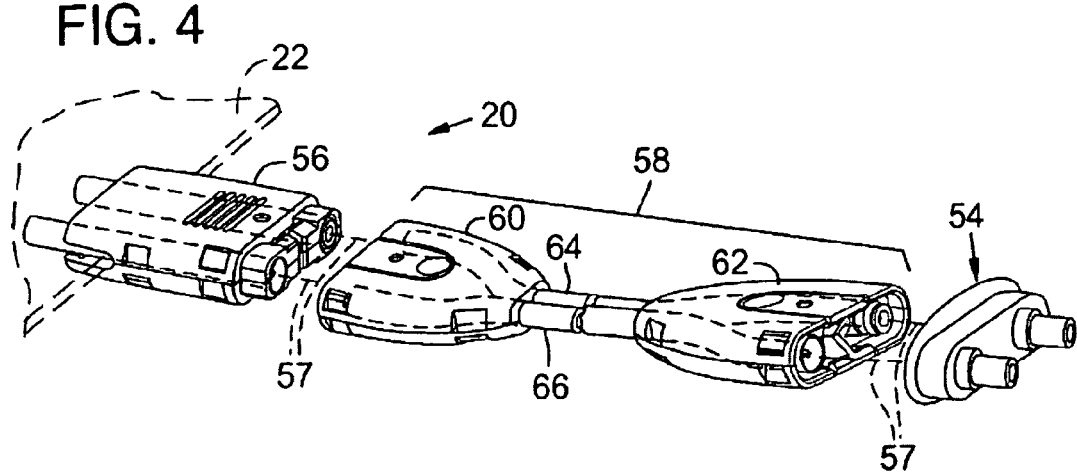
FIG. 4 is an isometric view of a fluidic coupling assembly in accordance with an embodiment of the present invention.

The Therapeutic Cranial Wrap 920 including Contrast Therapy System 10 may include the Fluidic Coupling Assembly 20 to selectively couple and decouple the Portable Control Unit 30 and the Therapy Pad 22 or, in the present invention, the Hood Shaped Therapy Pad 922. As shown in FIG. 4, the Fluidic Coupling Assembly 20 usually includes a Bulkhead 54, which is in fluid communication with the Mixing Valve 16, a wrap Connector 56 in fluid communication with the Cranial Contrast Therapy Bladder 1100, and a Reversible Tubing Assembly 58 for linking the Bulkhead 54 to the Connector 56. The Reversible Tubing Assembly 58 includes a First Tube-Set Connector 60 and a Second Tube-Set Connector 62 that are functionally equivalent to one another. Of course the First Tube-Set Connector 60 and the Second Tube-Set Connector 62 may be designed to differ from one another to limit connectivity as desired. First Tube-Set Connector 60 and Second Tube-Set Connector 62 are linked by Fluid Paths 64 and 66.

Bulkhead 54, First Tube-Set Connector 60, Second Tube-Set Connector 62, and Connector 56 each include one male valve and one female valve, which are configured to mate with a corresponding female and male valve, for example, as shown by dotted lines 40 in FIG. 4. The Bulkhead 54 and the Connector 56 are each configured to releasably receive either the First Tube-Set Connector 60 or the Second Tube-Set Connector 62. Therefore, Tubing Assembly 58 is completely reversible. For example, the Bulkhead 54 and the First Tube-Set Connector 60 may be coupled so that the Bulkhead's 54 male valve mates with the First Tube-Set Connector's 60 female valve, and the Bulkhead's 54 female valve mates with the First Tube-Set Connector's 60 male valve. Likewise, the Connector 56 and the Second Tube-Set Connector 62 may be coupled so that the bladder Connector's 56 male valve mates with the Second Tube-Set Connector's 62 female valve, and the bladder Connector's 56 female valve mates with the Second Tube-Set Connector's 62 male valve. Because the tubing assembly is reversible, the above described connection may be reversed. For example, if the First Tube-Set Connector 60 is connected to the Bulkhead 54, the Second Tube-Set Connector 62 is available for connection to the Connector 56, but if the Second Tube-Set Connector 62 is connected to the Bulkhead 54, the First Tube-Set Connector 60 is available for connection to the bladder Connector 56. In either case, such arrangements permit fluid to flow from the Portable Control Unit 30 to the Cranial Contrast Therapy Bladder 1100, and then return back to the Portable Control Unit 30.

The male and female valves of each of the above described components are equally spaced from one another. Therefore, male and female valves from one component may align with female and male valves from a corresponding component. Furthermore, Bulkhead 54 is complementarily configured relative to both the First and Second Tube-Set Connectors 60, 62 to facilitate securing either the First Tube-Set Connector 60 or the Second Tube-Set Connector 62 to the Bulkhead 54. Similarly, either the First Tube-Set Connector 60 or the Second Tube-Set Connector 62 may be secured to the bladder Connector 56. The male and female valves are designed to prevent fluid flow unless they are mated with one another, thus limiting leakage when disconnecting the Reversible Tubing Assembly 58 from the Portable Control Unit 30 and/or the Hood Shaped Therapy Pad 922.

The configuration of the Fluidic Coupling Assembly 20 facilitates easy connection and disconnection of a plurality of Portable Control Units 30, Tubing Assemblies 58, Hood Shaped Therapy Pad 922 and/or other thermal Therapy Pads 22. For example, the same Portable Control Unit 30 may be used with a variety of different Therapy Pads 22, which may be individually configured to treat different areas of a recipient's body. Similarly, Hood Shaped Therapy Pad 922 incorporated in a Therapeutic Cranial Wrap 920 may be used with a variety of different Portable Control Units 30, for example, when a recipient moves from one therapy location to another. The Fluidic Coupling Assembly 20 facilitates quick and easy coupling and decoupling, and the leak reducing male and female valves help limit spillage during such coupling and decoupling.

IV. Therapy Pad

Figure 5:
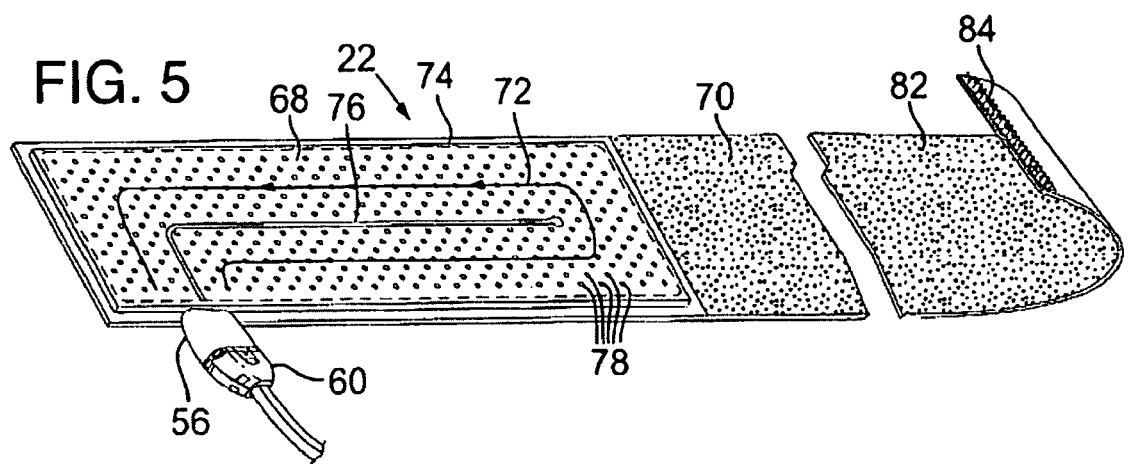
FIG. 5 is an isometric view of a contrast therapy pad in accordance with an embodiment of the present invention.

FIG. 5 shows Therapy Pad 22 apart from the remainder of the contrast therapy system. As described above, the Therapy Pad 22 may be easily coupled and decoupled from the Reversible Tubing Assembly 58, which allows various different Therapy Pads 22 to be used with the same control unit. Each Therapy Pad 22 is designed to receive therapy fluid from the mixing valve, such as through the fluidic coupling assembly, and return the therapy fluid to at least one of the hot reservoir and the cold reservoir (as shown schematically in FIG. 2). The Therapy Pad 22 returns fluid to the control unit, and the returned fluid may be recirculated. Depending on the type of therapy being applied, returned fluid may be heated and/or cooled at the control unit. The contrast therapy system may include a return valve that selectively directs return fluid to the hot reservoir and/or the cold reservoir, or the return fluid may be allowed to naturally flow to the lower pressure region.

Figure 6:
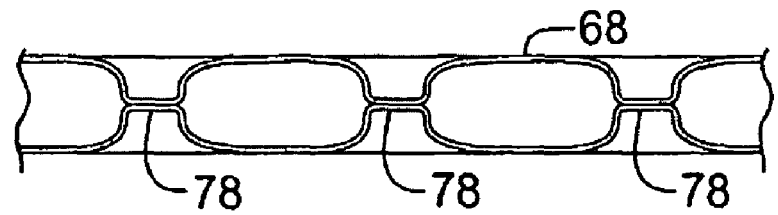
FIG. 6 is a cross-sectional view of a portion of the contrast therapy pad of FIG. 5.

In some embodiments, the Therapy Pad 22 includes an active Thermal Exchange Bladder 68 and an Elastic Wrap 70 that is connected to the Thermal Exchange Bladder 68. The Thermal Exchange Bladder 68 may include a flexible membrane of opposing faces that are welded together to define a channel system for directing the flow of therapy fluid along a desired Fluid Path 72 within the Thermal Exchange Bladder 68. For example, the faces are usually welded along a common Outer Perimeter 76, sealing the faces together. A division weld 76 may direct fluid through a substantial portion of the pad before returning to the control unit. The Thermal Exchange Bladder 68 may also include a plurality of Intermittent Welds 78 that limit inflation of the bladder, as shown in FIG. 6, which is a cross-sectional view of a portion of the exchange bladder.

The Thermal Exchange Bladder 68 facilitates thermal exchange between a therapy site and the therapy fluid. For example, when a cold therapy is administered, heat from a recipient's body may heat the therapy fluid, which in turn cools the therapy site. Similarly, when a hot therapy is administered, the therapy fluid may transfer heat to the therapy site. The therapy may be enhanced by moistening the bladder to provide a moist therapy. Furthermore, the fluid may also be pulsed through the bladder, adding a therapeutic massage aspect to the treatment.

In the illustrated embodiment, Therapy Pad 22 is dimensioned to hold approximately 26 cubic centimeters of fluid. However, the volume of the Therapy Pad 22 may be controlled by changing the size of the Therapy Pad 22, and/or the amount of inflation the intermittent welds allow. Furthermore, the Therapy Pad 22 may be constructed from an at least partially elastic material, such as urethane, which may permit the volume to change in response to the pressure of fluid within the bladder. In some embodiments, the bladder may include a less elastic material that helps prevent stretching, such as a vinyl/urethane blend.

As shown in FIG. 5, fluid may enter the bladder at bladder Connector 56, flow around the division weld and the Intermittent Welds 78, and leave the bladder at the bladder Connector 56. It is within the scope of the invention to reconfigure the bladder to accommodate different flow paths. For example, the division weld, or plural division welds, may be used to direct the fluid through a series of switchbacks before returning to the output of the bladder Connector 56. Small breaks may be included in the division weld to permit alternative flow paths if a primary flow path is blocked.

Figure 7:
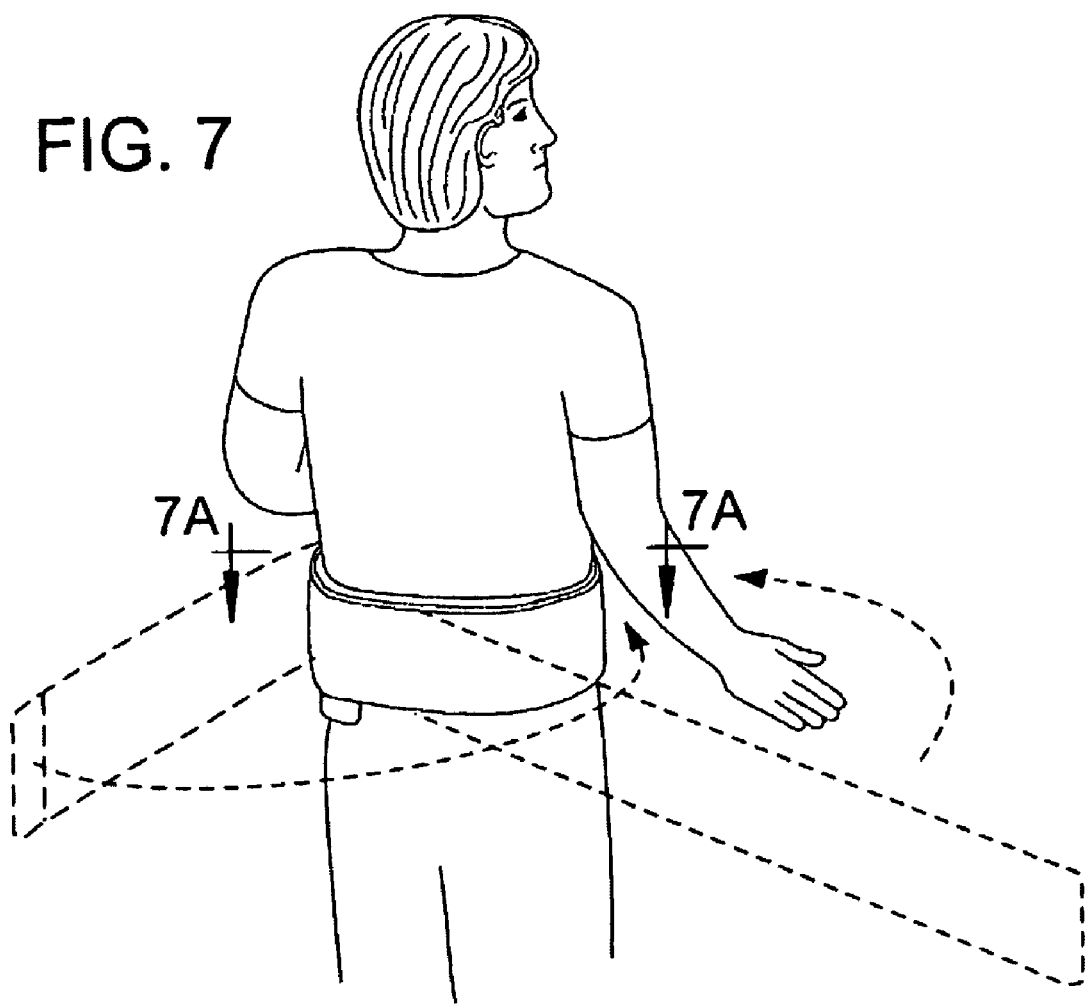
FIG. 7 is an isometric view of a therapy pad wrapped around a therapy recipient.

Elastic Wrap 70 is shown connected to the Thermal Exchange Bladder 68. The Elastic Wrap 70 may be configured to adjustably wrap around the Thermal Exchange Bladder 68 and compress the Thermal Exchange Bladder 68 around a therapy site. Compression helps induce contact of the bladder with the therapy site, which may promote efficient and even thermal transfer. Furthermore, the wrap is a compressive element in and of itself. When used in conjunction with the bladder, it keeps the bladder in contact with the therapy site, and it may also help reduce swelling through its own inherent compressibility. The wrap is continuously adjustable, meaning it may be repeatedly tightened and loosened to various levels of compression, as shown in FIG. 7. The wrap may be used in tandem with the bladder to wrap a therapy site in a variety of ways, thus providing extreme flexibility in the types of treatments that may be administered to a wide range of different therapy sites.

Wrap 70 is elastic; it may be stretched and naturally return to an unstretched disposition. When stretched, the wrap is at an increased tension, which may be used to compress a Therapy Pad 22 around a therapy site, as shown in FIG. 7A. Force vectors 80 schematically represent the compressive force resulting from the wrap. The magnitude of the compressive force may be selected by adjusting the amount the wrap is stretched. As the wrap is increasingly stretched around a therapy site, the compressive force the wrap applies increases. Similarly, the wrap may be loosened, decreasing the magnitude of the compressive force. The amount of elasticity a particular wrap has may be selected according to a desired application, or range of applications. In some embodiments, the wraps are designed to stretch to approximately 150%-200% of their unstretched length, however less elastic and more Elastic Wraps 70 may be used. The wraps may be variously sized, and are usually at least as long as their corresponding bladder when unstretched. As illustrated in FIG. 5, the unstretched wrap is six times as long (54 inches) as the bladder (18 inches). Because of the elastic configuration of the wrap, wrapping techniques known to physical therapists, physical trainers, and sports physicians may be used in conjunction with the Therapy Pad 22 to achieve a wide variety of therapeutic benefits.

As shown in FIG. 5, Elastic Wrap 70 is permanently connected to Thermal Exchange Bladder 68. The wrap may be connected by stitching, an adhesive, and/or another suitable fastener. In some embodiments, the bladder is connected to the wrap via an optional mesh envelope, shown in dashed lines at 69. In such embodiments, the envelope may be permanently connected to the wrap, and the bladder may be selectively positioned within the mesh envelope. The mesh envelope may include a fastening face configured to selectively fasten with a complimentary fastener of the wrap. The wrap may alternatively be removably connected to the bladder, such as by hook and loop connectors. By permanently connecting the wrap to the bladder, such as by stitching or configuring an envelope to securely hold the bladder relative to the wrap, the wrap and the bladder may cooperate to provide a compressive force, as described herein. Furthermore, the combination has proven to be much easier to apply than separated Therapy Pads and wraps, and thus is more versatile.

The wrap usually includes a surface of loops 82 that are adapted to detachably receive complementary hooks 84. The hooks and loops are positioned, so that the hooks may engage the loops when the wrap is wrapped around a therapy site, as shown in FIGS. 7 and 7A. The wrap may be adjusted to a desired tension and a corresponding level of compressive force that may be fixed by engaging the hooks and the loops together. The hooks and loops may subsequently be disengaged, so that the tension may be adjusted, for instance, and reengaged at will. In some embodiments, a wrap lock may alternatively be used to secure the wrap.

In some embodiments, the Therapy Pads 22 may be constructed with disposable materials. For example, pads configured for a single use may be constructed from disposable materials, which are usually less expensive than reusable materials. Disposable Therapy Pads 22 may be particularly useful in emergency, trauma, or post surgery situations, in which a therapy recipient may bleed onto the Therapy Pad 22. The ability to control the temperature of the Therapy Pad 22, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

Figure 8:
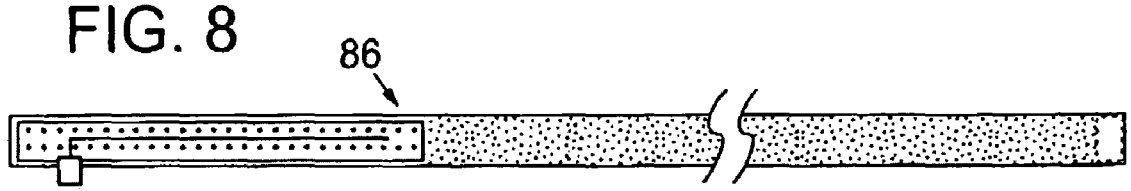
FIG. 8 is a plan view of a contrast therapy pad in accordance with an embodiment of the present invention.

The Thermal Exchange Bladder 68 may be sized and shaped according to a particular range of applications. For example, a 6 inch by 18 inch bladder (as shown at 22 in FIG. 5) may be useful in treating backs, legs, arms, shoulders, and other therapy sites. Although the versatile configuration of Therapy Pad 22 may be used for virtually any therapy site, other Therapy Pads 22 may be configured to even better accommodate particular therapy sites. For example, a 2 inch by 18 inch Bladder 86, as shown in FIG. 8, may be particularly useful for treating smaller therapy sites, such as hands, wrists, feet, ankles, etc. Similarly, a shoulder Therapy Pad 22 may be designed to intimately engage a shoulder therapy site, thus providing comfortable and improved treatment. A jaw Therapy Pad 22, which is useful in treating the facial area, may be designed to comfortably wrap around a head, while positioning a bladder in contact with at least one side of a jaw. It should be understood that the above Therapy Pads are provided as examples, and other Therapy Pads may also be used. Furthermore, each Therapy Pad 22 may include a suitable Elastic Wrap 70 and/or other fastening mechanism.

The therapy system may be used to treat a wide range of conditions, including injured muscles, bones, joints, tendons, ligaments etc. Furthermore, other conditions may be treated, such as mastitis, breasts that are sore from menstruation, and headaches. The therapy system may also be used as a preventative remedy, for example the therapy system may be used during child birth to help alleviate discomfort during labor as well as help minimize resulting soreness and/or discomfort. For example, providing a cold treatment to a recipient's back during child birth may help cool the recipient, thus alleviating immediate discomfort, as well as subsequent soreness.

V. Therapeutic Cranial Wrap

Figure 9:
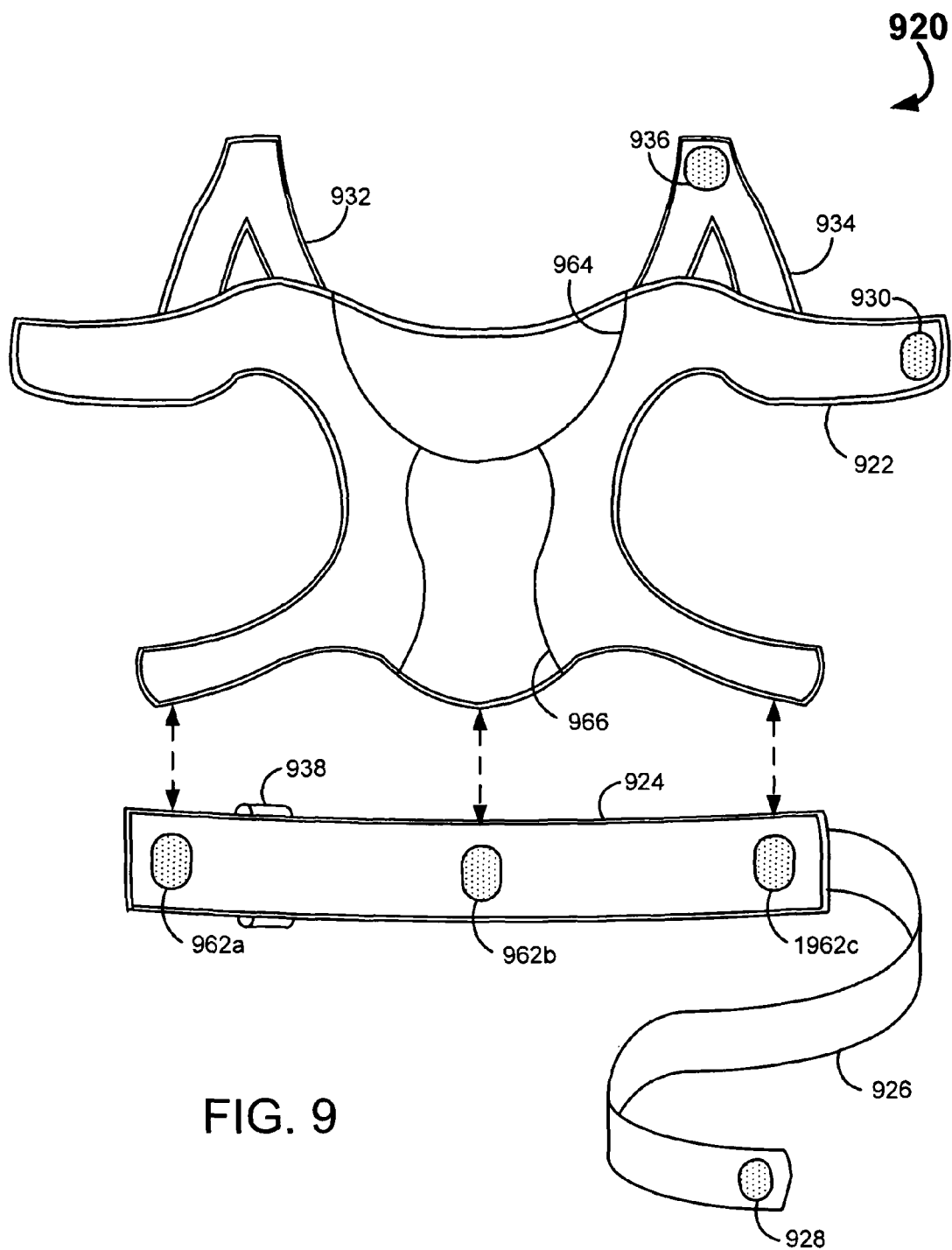
FIG. 9 is an illustration of the cranial wrap in an open position in accordance with an embodiment of the present invention.

FIG. 9 is an illustration of the Therapeutic Cranial Wrap 920 in an open position. Here the Hood Shaped Therapy Pad 922 and Neck Compress 924 are shown as separate units; however, as will be discussed below, the Hood Shaped Therapy Pad 922 and Neck Compress 924 may be a single piece. The advantage of having two pieces may include ease of cleaning and a more customized fit. The Neck Compress 924 may couple to the Hood Shaped Therapy Pad 922 via one or more Hook Material Coupler Sites 962a, 962b and 962c.

The Hood Shaped Therapy Pad 922 may include a unique design including a Head Cradle Contour 964 and a Neck Contour 966. The Head Cradle Contour 964 and Neck Contour 966 ensure that the Hood Shaped Therapy Pad 922 contours to the head and neck of the Therapy Recipient 910 in a snug fashion. Since the Cranial Contrast Therapy Bladder 1100 is housed in the Hood Shaped Therapy Pad 922, this form fitting enables efficient thermal transfer from the thermal fluid to the therapy sites of the Therapy Recipient 910.

Headaches in the frontal lobe are categorical pains usually affecting the head. The pain spreads to areas above the eyes or the ears and sometimes at the back portion of the upper neck as well. These type of headaches are either primary or secondary in nature. Migraine headaches, tension headaches and cluster headaches are three popular primary varieties.

Tension headaches and cluster headaches focus along the frontal lobe or above the eyes. Migraine is more in the occipital lobe or the back of the head. The Therapeutic Cranial Wrap 920 is designed to cover these areas, be very adjustable given the head type and to allow for hair to be routed out of the way.

Figure 12A:
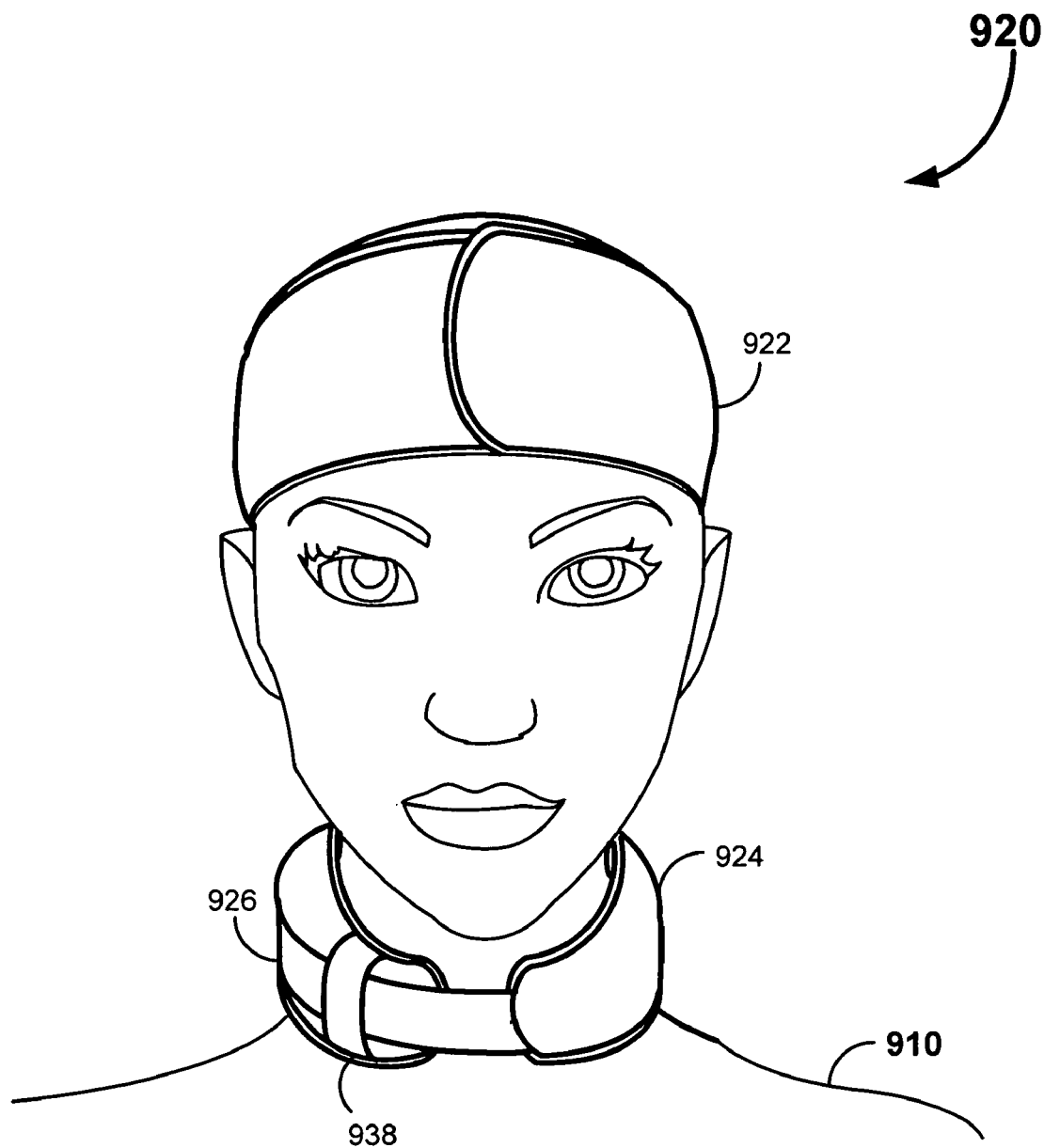
FIG. 12A is a frontal view illustration showing the application of the cranial wrap, in a secured position, to the therapy recipient in accordance with an embodiment of the present invention.

FIG. 12A is a frontal view illustration showing the application of the Therapeutic Cranial Wrap 920, in a secured position, to the Therapy Recipient 910. The Therapeutic Cranial Wrap 920 includes a Hood Shaped Therapy Pad 922 which extends around the head of the Therapy Recipient 910. The Hood Shaped Therapy Pad 922 may be capable of adjustment and may be made from elastic material. The amount of elasticity a particular Hood Shaped Therapy Pad 922 has may be selected according to a desired application, or range of applications. In some embodiments, the Hood Shaped Therapy Pad 922 is designed to stretch to approximately 150%-200% of their unstretched length, however less elastic and more elastic Hood Shaped Therapy Pad 922 may be used. Such elasticity may provide some compression; however, the primary purpose for an elastic Hood Shaped Therapy Pad 922 is to provide maximal contact along pain points of the therapy recipient.

The Hood Shaped Therapy Pad 922 may be variously sized, and are usually at least as long as required to wrap around the head of the Therapy Recipient 910 in order to secure the Therapeutic Cranial Wrap 920 to the therapy site. The Hood Shaped Therapy Pad 922 usually includes a surface of loops that are adapted to detachably receive complementary hooks. The hooks and loops are positioned so that the hooks may engage the loops when the Hood Shaped Therapy Pad 922 is wrapped around the wearer's head. The Hood Shaped Therapy Pad 922 may be adjusted to a desired tension and may be fixed by engaging the hooks and the loops together. The hooks and loops may subsequently be disengaged, so that the tension may be adjusted, for instance, and reengaged at will. In some embodiments, a wrap lock, zipper, button, or other appropriate system may alternatively be used to secure the Therapeutic Cranial Wrap 920 to the head of the Therapy Recipient 910.

The Therapeutic Cranial Wrap 920 may extend down the back of the head and neck of the Therapy Recipient 910. At the base of the Therapeutic Cranial Wrap 920 is the Neck Compress 924. In some embodiments, the Neck Compress 924 is a separate piece designed to engage the Hood Shaped Therapy Pad 922. Separate pieces allows for more customized fitting and support. Likewise, a detachable Neck Compress 924 may aid in cleaning the Therapeutic Cranial Wrap 920.

The Neck Compress 924 may include padding to aid in neck support for the Therapy Recipient 910. Additionally, the Neck Compress 924 may efficiently hold the thermal bladder of the Therapeutic Cranial Wrap 920 in a tight and secure position against the curve of the neck.

The Neck Compress 924 may be secured to the Therapy Recipient 910 by means of a Collar Band 926. The Collar Band 926 may be elastic. Also, the Collar Band 926 may be secured in any of the methods described above. However, in some embodiments, the fastener for the Collar Band 926 may be designed to disengage at a particular tension in order to prevent choking or an uncomfortable fit. The Collar Band 926 may be extended through a Loop 938 in order to ensure proper fit and minimize slippage of the Collar Band 926.

Figure 12B:
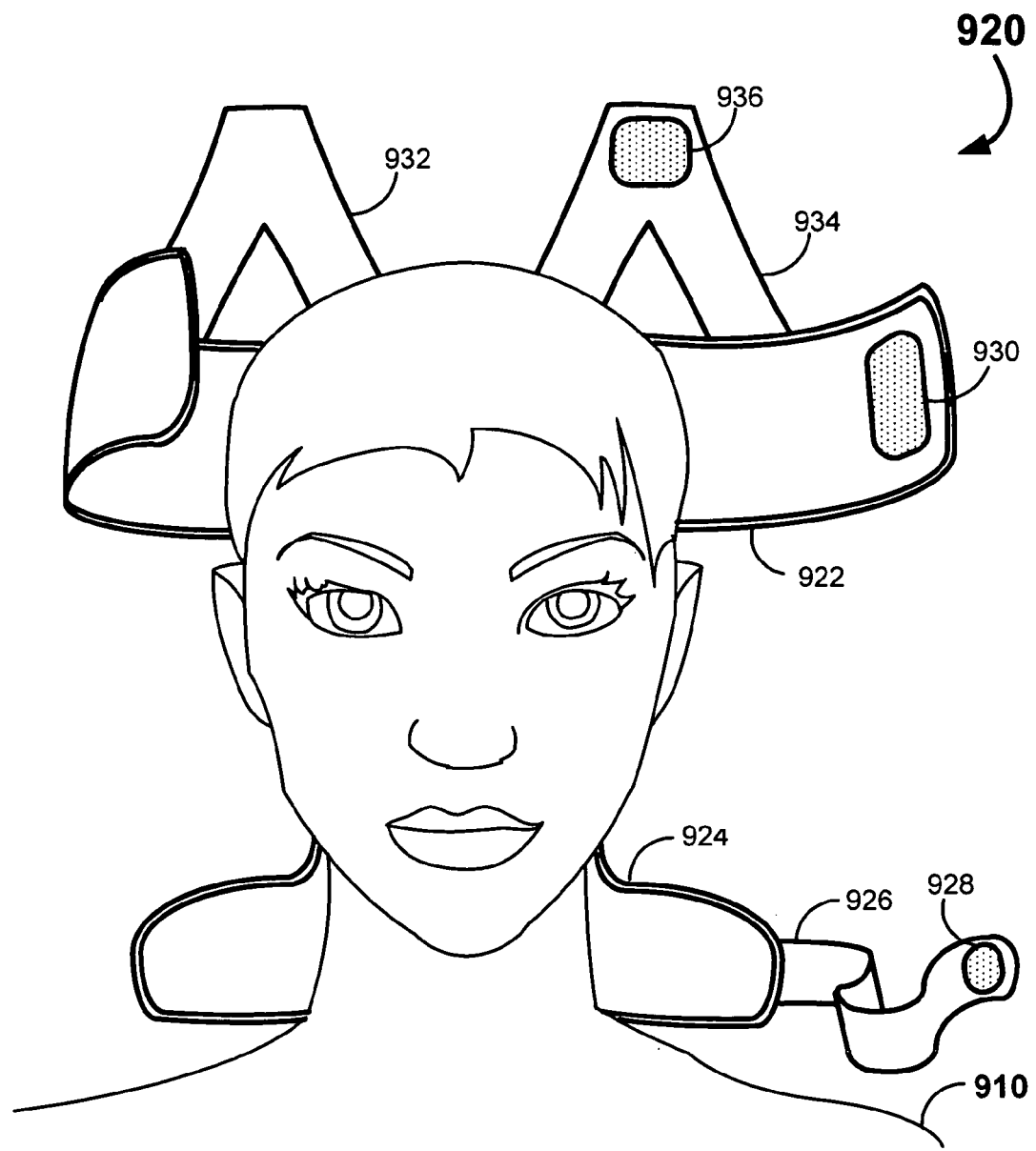
FIG. 12B is a frontal view illustration showing the application of the cranial wrap, in an open position, to the therapy recipient in accordance with an embodiment of the present invention.

FIG. 12B is another frontal view illustration showing the application of the Therapeutic Cranial Wrap 920, in an open position, to the Therapy Recipient 910. Again the Hood Shaped Therapy Pad 922 may be seen; however, in this illustration the First Dorsal Strap 932 and Second Dorsal Strap 934 are additionally visible. The First Dorsal Strap 932 and Second Dorsal Strap 934 may be separate from the Hood Shaped Therapy Pad 922 or may be permanently joined to the Hood Shaped Therapy Pad 922. In some embodiments, a single piece includes the Hood Shaped Therapy Pad 922, First Dorsal Strap 932 and Second Dorsal Strap 934.

The First Dorsal Strap 932 and Second Dorsal Strap 934 couple on the top of the head of the Therapy Recipient 910. First Dorsal Strap 932 and Second Dorsal Strap 934 may be made of elastic material as to enable a customizable and snug fit. A Dorsal Hook Material Pad 936 may function to couple the Second Dorsal Strap 934 to the First Dorsal Strap 932. Likewise, the Main Hook Material Pad 930 may be readily seen in the present illustration. In some embodiments, the entire surface of the Hood Shaped Therapy Pad 922 may consist of loop-like material, thereby enabling the Main Hook Material Pad 930 to releasably couple to the Hood Shaped Therapy Pad 922 at virtually any location. In some alternate embodiments, loop pads (not shown) may be provided on the surface of the Hood Shaped Therapy Pad 922 to provide specific points of contact for the Main Hook Material Pad 930. Likewise, the Collar Band 926 as previously noted may have a Collar Hook Material Pad 928 designed to couple to the Neck Compress 924.

The dorsal straps may be fashioned as to have open spaces along the top of the head when coupled together. These spaces enable the head to 'breath', limit moisture accumulation and enable the wearer to rout her hair out from under the wrap. Thus, even therapy recipients with long hair may use the present wrap comfortably.

Figure 10A:
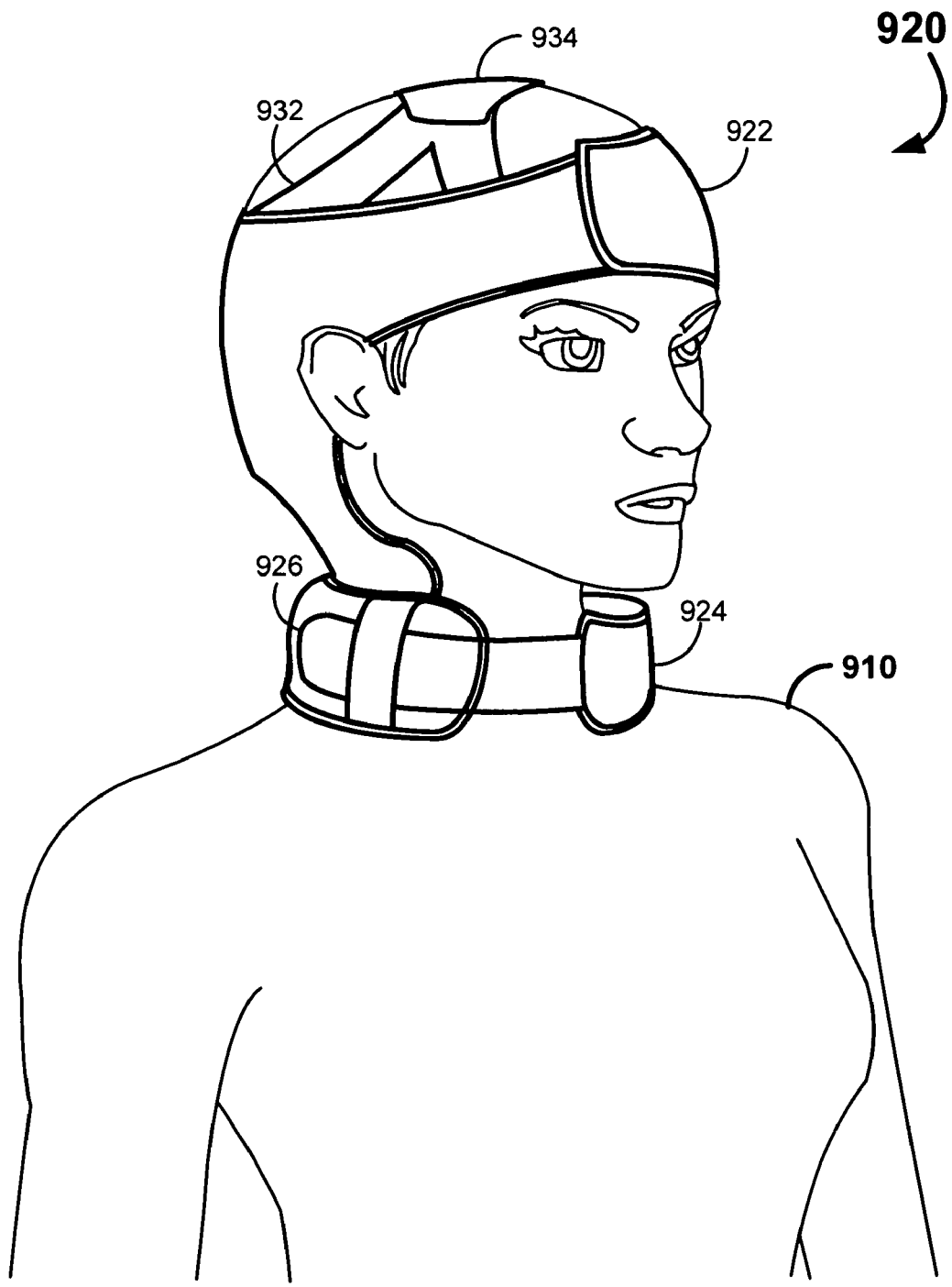
FIG. 10A is a side view illustration showing the application of the cranial wrap, in a secured position, to the therapy recipient in accordance with an embodiment of the present invention.
Figure 10B:
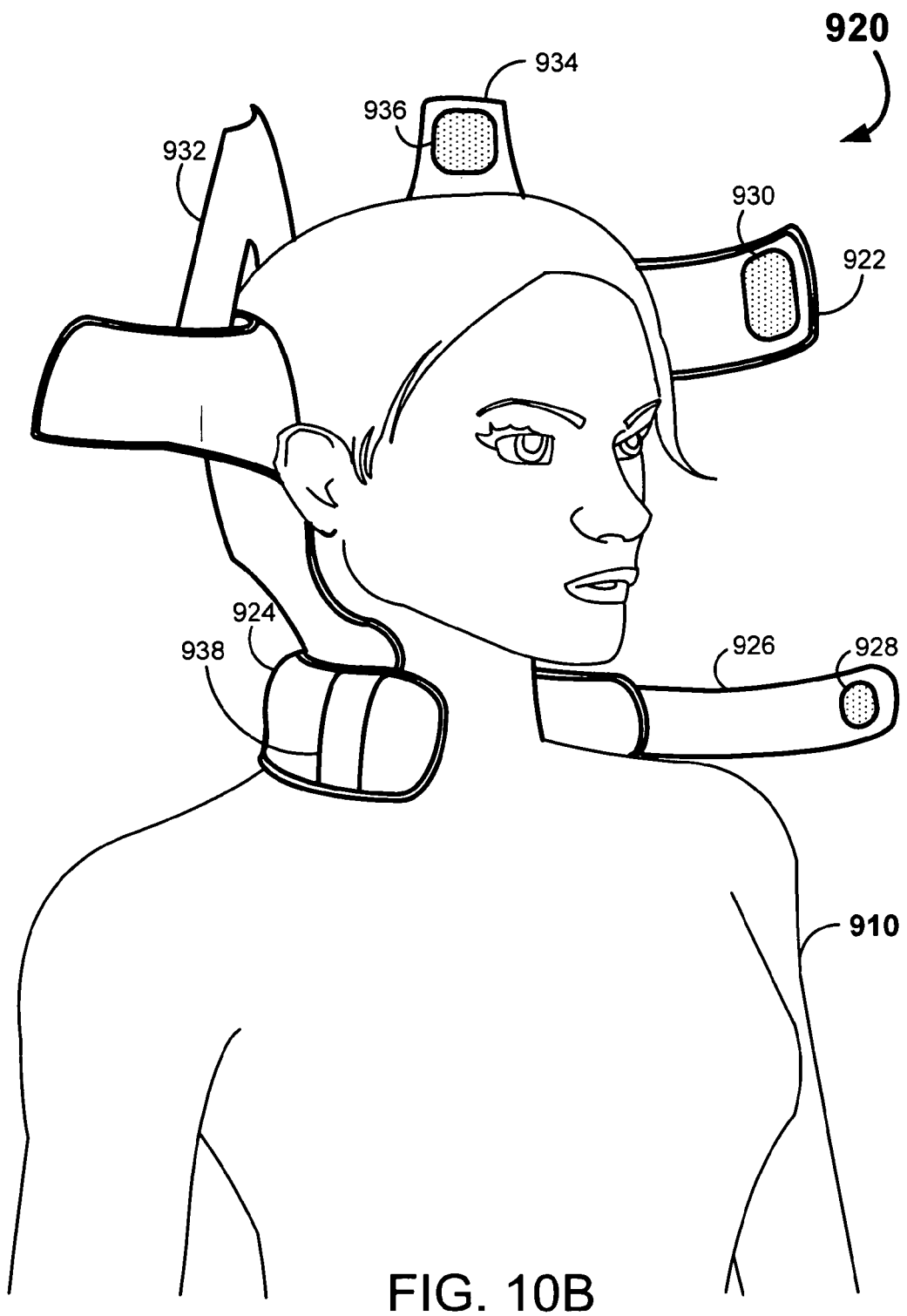
FIG. 10B is a side view illustration showing the application of the cranial wrap, in an open position, to the therapy recipient in accordance with an embodiment of the present invention.

FIGS. 10A and 10B are side view illustrations showing the application of the Therapeutic Cranial Wrap 920 to the Therapy Recipient 910. In these illustrations the First Dorsal Strap 932 and Second Dorsal Strap 934 may be more readily seen. Additionally, the fit of the Hood Shaped Therapy Pad 922 on the Therapy Recipient 910 may be seen with better detail.

As previously noted, the Hood Shaped Therapy Pad 922 extends down the head and neck of the Therapy Recipient 910 and couples to the Neck Compress 924 at the base of the neck of the Therapy Recipient 910. The Hood Shaped Therapy Pad 922 may include ergonomic padding which may line the interior of the Therapeutic Cranial Wrap 920. Padding may couple to the Therapeutic Cranial Wrap 920 to provide pin-point cushioning along likely pressure points without hindering neck or jaw movement. Alternatively, padding may be worn as a separate layer beneath the Therapeutic Cranial Wrap 920. Padding may include separate pads, or may be a single sheath. In some embodiment, the padding may be included in the Therapeutic Cranial Wrap 920, or the Therapeutic Cranial Wrap 920 may be sufficiently contoured, or of sufficiently flexible material, to warrant no padding. Padding may also provide some degree of neck support. In some embodiments, the Hood Shaped Therapy Pad 922 may additionally include rigid members to provide stiffer neck support (not shown). Likewise, in some embodiments, the Therapeutic Cranial Wrap 920 may be incorporated within a rigid neck brace, or may be worn beneath such neck braces. Such "support style" cranial wraps may be useful for therapy recipients who have sustained a neck injury. However, for a typical migraine wrap, such support features are unnecessary and often not desired due to limitations on mobility and increased wrap bulk.

When in the open position, the Therapeutic Cranial Wrap 920 may be seen as easily donned. The Collar Hook Material Pad 928, Main Hook Material Pad 930 and Dorsal Hook Material Pad 936 may be attached to accommodate virtually any head shape or size.

Figure 11:
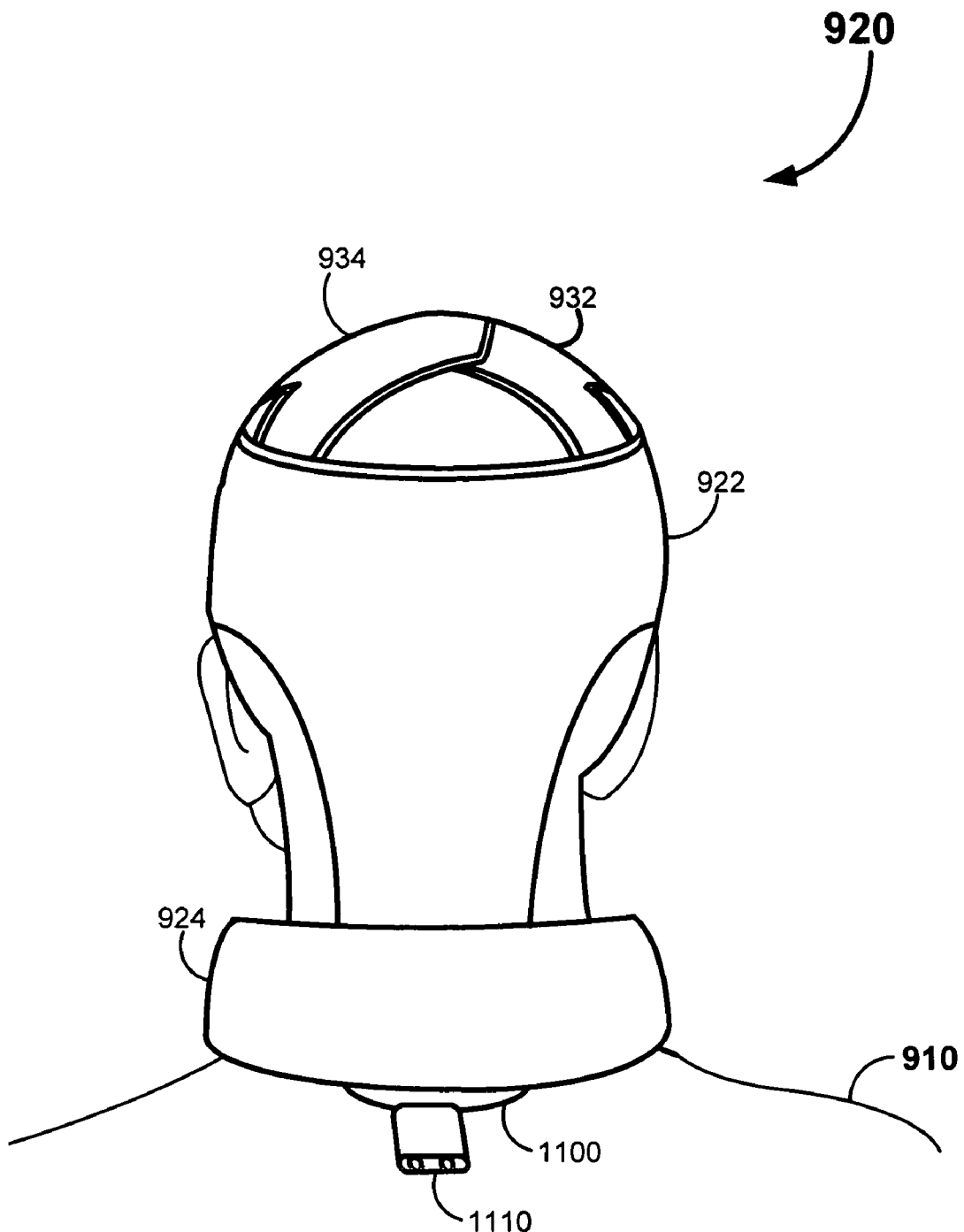
FIG. 11 is a rear view illustration showing the application of the cranial wrap, in a secured position, to the therapy recipient in accordance with an embodiment of the present invention.

FIG. 11 is a rear view illustration showing the application of the Therapeutic Cranial Wrap 920, in a secured position, to the Therapy Recipient 910. Again, the First Dorsal Strap 932 and Second Dorsal Strap 934 may be readily seen coupled at the top of the head of the Therapy Recipient 910. Spacing for hair routing may be easily seen from this view.

The Hood Shaped Therapy Pad 922 extends down the back of the head and neck of the Therapy Recipient 910. Padding or rigid members, as discussed above, may be incorporated within the Hood Shaped Therapy Pad 922 to provide neck support to the Therapy Recipient 910. Likewise, for a migraine wrap, such padding or supports may be omitted for a sleeker look and added wear-ability.

A Cranial Contrast Therapy Bladder 1100 may be seen extending from below the Neck Compress 924. The Neck Compress 924 holds the Cranial Contrast Therapy Bladder 1100 securely against the neck of the Therapy Recipient 910. Likewise, a Bladder Coupler 1110 couples to the Cranial Contrast Therapy Bladder 1100 and provides a point of connection for the contrast therapy fluid coupler.

Figure 13:
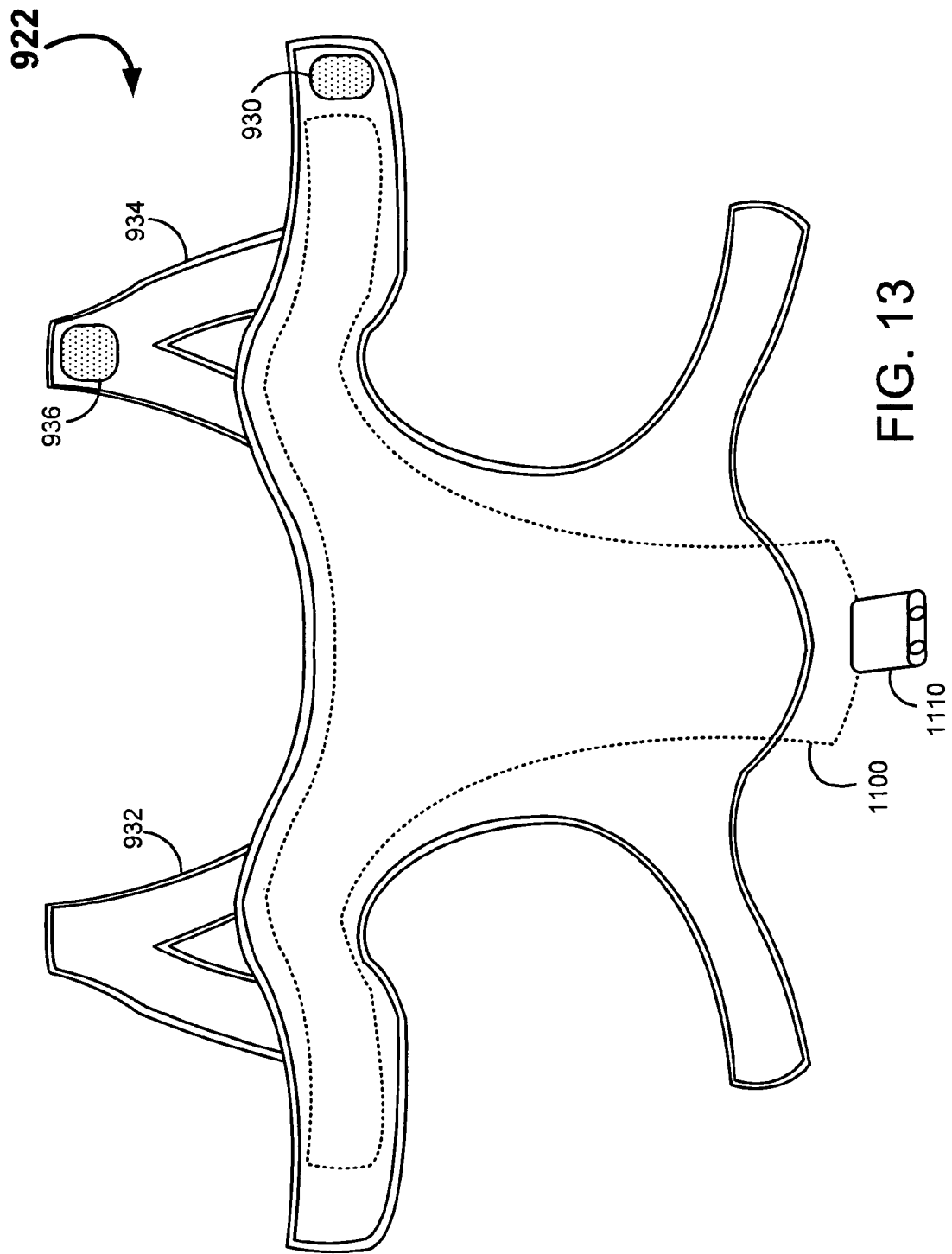
FIG. 13 is an illustration of the cranial wrap in an open position showing the active thermal bladder location in accordance with an embodiment of the present invention.
Figure 14A:
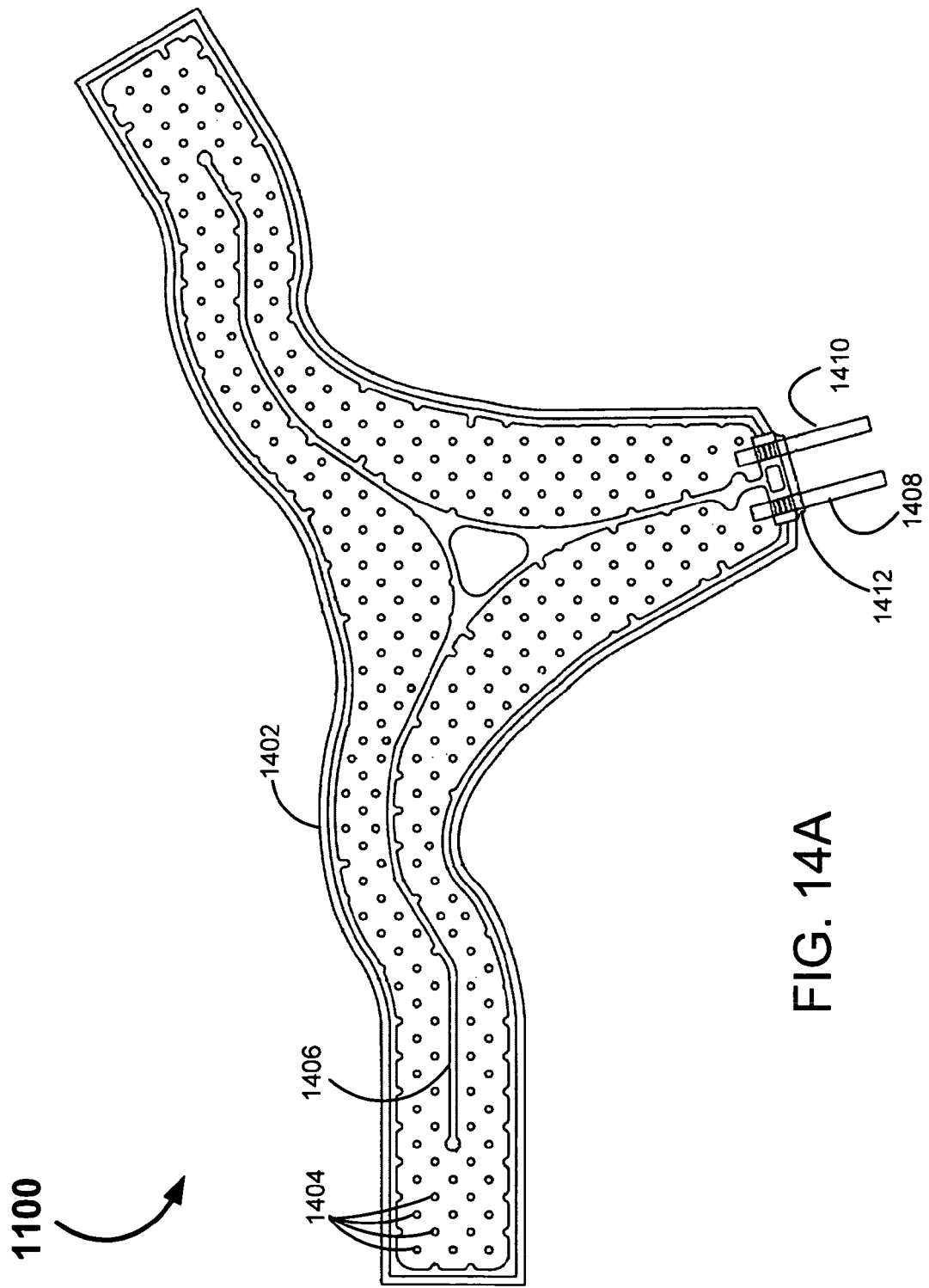
FIG. 14A is an illustration of the thermal bladder of the cranial wrap in accordance with an embodiment of the present invention.

FIG. 13 is an illustration of the Hood Shaped Therapy Pad 922 in an open position showing the location of the Cranial Contrast Therapy Bladder 1100. As may be seen, the Cranial Contrast Therapy Bladder 1100 extends up from the nap of the neck to the back of the head of the Therapy Recipient 910. The Cranial Contrast Therapy Bladder 1100 further extends into the "arms" of the Hood Shaped Therapy Pad 922 which circumvents the head of the Therapy Recipient 910. Thus, thermal therapy occurs along the back of the neck and head, and extends around the head to the forehead.

As noted above, headaches in the frontal lobe typically has pain which spreads to areas above the eyes or the ears and sometimes at the back portion of the upper neck as well. Note that the Cranial Contrast Therapy Bladder 1100 is designed to extend along these regions of pain, for maximal contrast therapy at the pain points.

The Bladder Coupler 1110 couples the Cranial Contrast Therapy Bladder 1100 to the fluidic coupler and ultimately to the contrast therapy system.

The Hood Shaped Therapy Pad 922 may include many layers. In some embodiments, the Hood Shaped Therapy Pad 922 may include an exterior layer which consists of loop-like material. This exterior may be easily cleaned and may have elastic properties. When donned, this exterior facing would be visible to observers of the Therapy Recipient 910. After the exterior layer may be padding, interfacing, boning, or any additional materials to enhance the comfort, fit and flexibility or rigidity of the Hood Shaped Therapy Pad 922. The primary purpose of this outer layer may be to ensure maximal fit of the Cranial Contrast Therapy Bladder 1100 to the pain points of the therapy recipient.

The next layer may include the Cranial Contrast Therapy Bladder 1100. Lastly, an interior layer may exist which contacts the Therapy Recipient 910 directly. In some embodiments, the interior layer may include a mesh material or other thermally conductive material. Additionally, the inner layer may be designed to be easily cleaned.

In some embodiments, the Hood Shaped Therapy Pad 922 may be made from entirely disposable materials. For example, pads configured for a single use may be constructed from disposable materials, which are usually less expensive than reusable materials. Disposable Hood Shaped Therapy Pad 922 may be particularly useful in emergency, trauma, or post surgery situations, in which a therapy recipient may bleed onto the Hood Shaped Therapy Pad 922. The ability to control the temperature of the Hood Shaped Therapy Pad 922, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

VI. Active Thermal Exchange Bladder

The novel design of the bladder of the instant invention allows for active or passive articulation of a therapy site while providing continuous thermal therapy and constant compression. FIG. 14A is an illustration of the Cranial Contrast Therapy Bladder 1100 of the Therapeutic Cranial Wrap 920.

The Cranial Contrast Therapy Bladder 1100 facilitates thermal exchange between a therapy site and the therapy fluid. For example, when a cold therapy is administered, heat from a recipient's body may heat the therapy fluid, which in turn cools the therapy site of the recipient's body. Similarly, when a hot therapy is administered, the therapy fluid may transfer heat to the therapy site. The therapy may be enhanced by moistening the Cranial Contrast Therapy Bladder 1100 to provide a moist therapy. Furthermore, the fluid may also be pulsed through the Cranial Contrast Therapy Bladder 1100, adding a therapeutic massage aspect to the treatment.

In the illustrated embodiment, Cranial Contrast Therapy Bladder 1100 may be dimensioned to hold approximately 200 cubic centimeters of fluid within the bladder Volume 1424. However, the Volume 1424 of the Cranial Contrast Therapy Bladder 1100 may be controlled by changing the size of the Cranial Contrast Therapy Bladder 1100, and/or the amount of inflation the Intermittent Welds 1404 allow. Furthermore, the Cranial Contrast Therapy Bladder 1100 may be constructed from an at least partially elastic material, such as urethane, which may permit the Volume 1424 to change in response to the pressure of fluid within the Cranial Contrast Therapy Bladder 1100. In some embodiments, the Cranial Contrast Therapy Bladder 1100 may include a less elastic material that helps prevent stretching, such as a vinyl/urethane blend. In some embodiment, the Cranial Contrast Therapy Bladder 1100 may be dimensioned to hold between 150 to 400 cubic centimeters of fluid within the bladder Volume 1424. This range of fluid volume provides the necessary balance between weight and thermal transfer.

As shown in FIGS. 14A and 14B, fluid may enter the Cranial Contrast Therapy Bladder 1100 at the Bladder Inlet 1408, flow around the Division Weld 1406 and the Intermittent Welds 1404, and leave the Cranial Contrast Therapy Bladder 1100 at the Bladder Outlet 1410. It is within the scope of the invention to reconfigure the Cranial Contrast Therapy Bladder 1100 to accommodate different Flow Paths 1450. For example, the Division Weld 1406, or plurality of division welds, may be used to direct the fluid through a series of switchbacks before returning to the Bladder Outlet 1410 of the Bladder Coupler Site 1412. Small breaks may be included in the Division Weld 1406 to permit alternative Flow Paths 1450 if a primary Flow Path 1450 is blocked.

The Cranial Contrast Therapy Bladder 1100 includes a matrix of Intermittent Welds 1404 which optimizes the distribution of fluid circulated in the bladder during therapy. Each of the plurality of Intermittent Welds 1404 is spaced along the matrix at a position which is equidistant from each other such weld. The matrix design evenly spaces the plurality of Welds 1404 within the matrix. The matrix is defined independently of the shape of the bladder into which it is to be incorporated. The equidistant nature of each Weld 1404 is maintained regardless of where the perimeter of the Cranial Contrast Therapy Bladder 1100 intersects the pre-defined matrix. As such, Welds 1404 may blend into the edges of the bladder as shown in FIGS. 14A and 14B.

The instant weld matrix has been found to help optimize the distribution of fluid, pressure and temperature throughout the Cranial Contrast Therapy Bladder 1100. The even temperature distribution gives the advantage of even application of thermal or contrast therapy at the neck and head therapy site. The even distribution of pressure throughout the Cranial Contrast Therapy Bladder 1100 aids in the application of constant compression at the therapy site. This feature is especially important since free head movement is desirous. Traditional thermal pads have a tendency to bunch and kink at critical sites in flexure. When under fluid pressure during the application of thermal therapy, traditional bladders tend to offer even more resistance to motion at these critical sites. The instant weld matrix configuration evenly distributes pressure throughout the Cranial Contrast Therapy Bladder 1100 allowing the Cranial Contrast Therapy Bladder 1100 to flex and extend more easily while delivering thermal and compressive therapy.

While the instant Hood Shaped Therapy Pad 922 eliminates bunching or kinking at critical sites, pressurized Cranial Contrast Therapy Bladders 1100 intrinsically offer resistance to motion. Internal bladder pressure exerts an outward force on the faces of the Cranial Contrast Therapy Bladder 1100 which must be overcome by an external force in order to move the Cranial Contrast Therapy Bladder 1100 through the desired range of motion. By evenly distributing the fluid and, by extension, the pressure throughout the Cranial Contrast Therapy Bladder 1100, the instant design minimizes the resistance of the Cranial Contrast Therapy Bladder 1100 to motion.

A Cranial Contrast Therapy Bladder 1100 is generally flat when it is in an open configuration, although the Cranial Contrast Therapy Bladder 1100 may be made from a flexible material, which allows the Cranial Contrast Therapy Bladder 1100 to be temporarily bent or otherwise flexed from a flat shape. In other words, the Cranial Contrast Therapy Bladder 1100 is not predisposed to have a concave shape, or similar three-dimensional shape. However, in some embodiments, the Cranial Contrast Therapy Bladder 1100 may be shaped with a concave inner contour in order to facilitate a close fit to a particular therapy site and increased contact between the Cranial Contrast Therapy Bladder 1100 and the therapy site, which may increase the effectiveness of applied therapies.

In some embodiment, the Cranial Contrast Therapy Bladder 1100 may be inflated as to press against the Therapy Recipient 910, thereby providing a compression therapy on the therapy site. The Pump 18 housed within the Portable Control Unit 30 may provide the fluid pressure required to inflate the Cranial Contrast Therapy Bladder 1100. By controlling the pressure within the Cranial Contrast Therapy Bladder 1100 the intensity of compression on the therapy site may be regulated. As such, the pressure within the Cranial Contrast Therapy Bladder 1100 may be held constant, thereby providing a steady compression on the therapy site. Alternatively, the pressure within the Cranial Contrast Therapy Bladder 1100 may be varied dynamically, thereby providing a therapeutic, massage-like pulsation on the therapy site. The Cranial Contrast Therapy Bladder 1100 may be inflated and subsequently depressurized in rapid succession to emulate a more rigorous vibrating therapy, or may be more slowly inflated and depressurized as is desirable. It may also be possible, in some embodiment, to provide very complicated compression cycles as is found to best suit the therapy recipients needs. Control over type and rate of compression therapy may be automated, or may be manually alterable.

Additionally, the Cranial Contrast Therapy Bladder 1100 may vary in shape and size in order to accommodate particular therapeutic desires or Therapeutic Cranial Wrap 920 configurations.

Figure 14C:
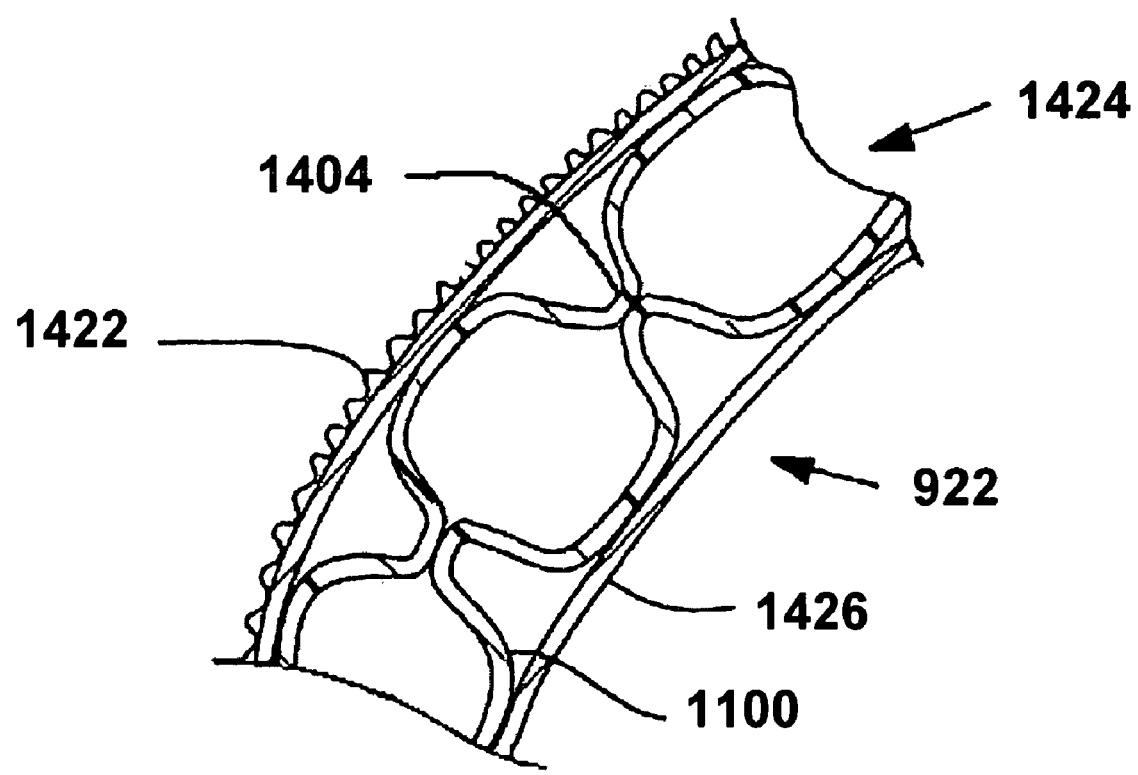
FIG. 14C is an exemplary first cross sectional illustration of the thermal bladder of the cranial wrap in accordance with an embodiment of the present invention.
Figure 15:
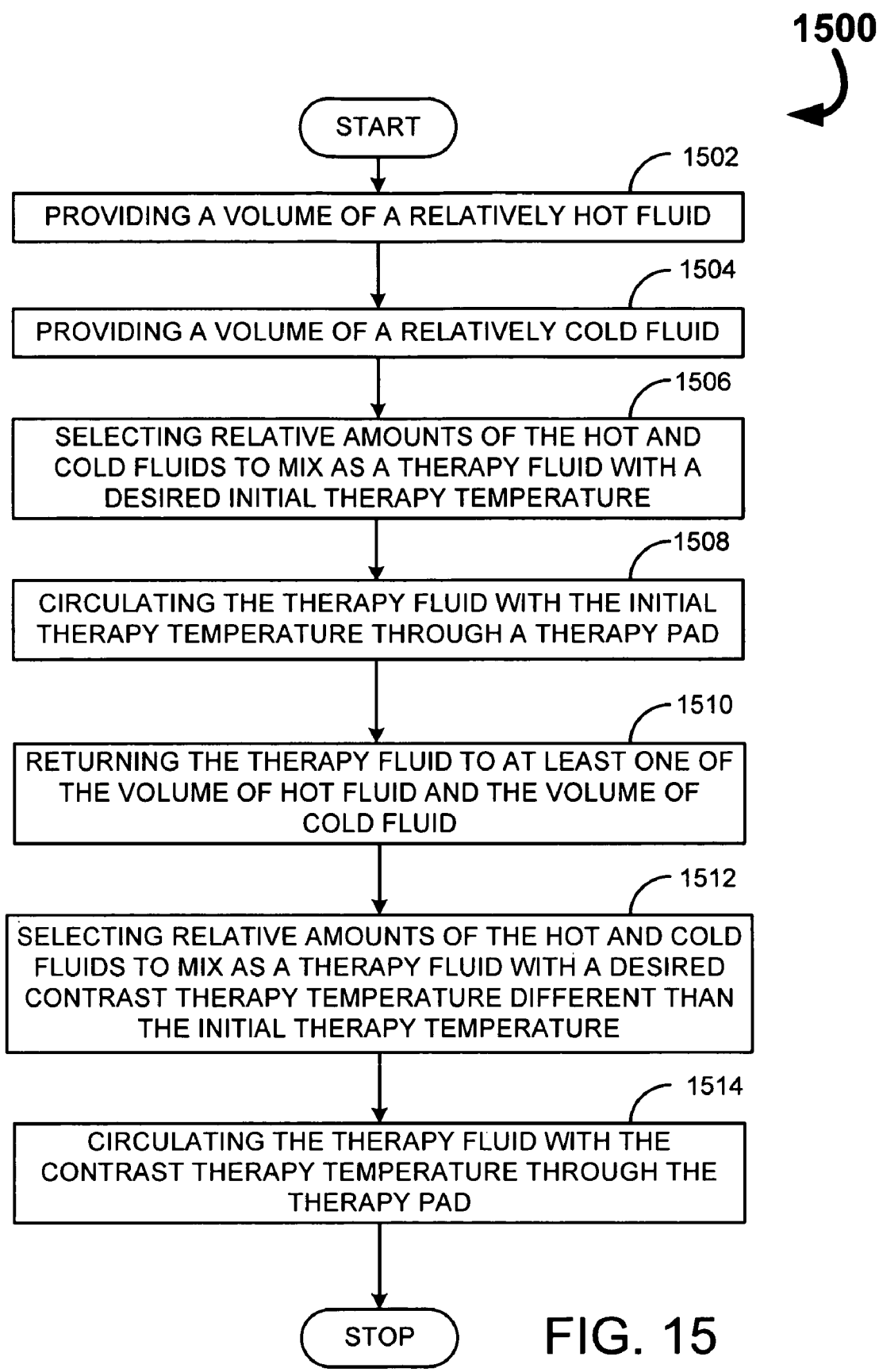
FIG. 15 is an illustration of a method for administering contrast therapy to a therapy recipient in accordance with an embodiment of the present invention.

FIG. 14C shows an exemplary first cross sectional illustration of the Cranial Contrast Therapy Bladder 1100 within the Hood Shaped Therapy Pad 922 of the Therapeutic Cranial Wrap 920. The Intermittent Welds 1404 provide strength to the Cranial Contrast Therapy Bladder 1100 as well as restrict the expansion of the Thermal Exchange Bladder's Volume 1424. The interior face is covered by Mesh 1426 that promotes thermal transfer to the therapy site. The exterior face of the bladder envelope includes Solid Material 1422 for enclosing the Cranial Contrast Therapy Bladder 1100, providing thermal insulation, and additional structural support for the Hood Shaped Therapy Pad 922. Loop material may be seen covering the Solid Material 1422 which provides a surface for coupling to the Main Hook Material Pad 930 and Dorsal Hook Material Pad 936.

Although not shown, a compression bladder may be included within the Therapeutic Cranial Wrap 920. A compression bladder connector allows for inflation of the compression bladder with air or other fluid.

The compression bladder may include a flexible membrane of opposing faces that are welded together to define a volume for pressurized expansion. For example, the faces are usually welded along a common outer perimeter, sealing the faces together. Also, like the Cranial Contrast Therapy Bladder 1100, the compression bladder may also include a plurality of intermittent welds that limit inflation of the bladder.

A pressurizing pump (not shown) supplies the pressurizing fluid through the compression bladder connector, and regulates the pressure within the compression bladder. The pressurizing fluid may include air, water or any other suitable fluid. The compression bladder may be inflated as to press against the Cranial Contrast Therapy Bladder 1100, which in turn presses against the therapy recipient, thereby providing a compression therapy on the therapy site. By controlling the pressure within the compression bladder, the intensity of compression on the therapy site may be regulated. Thus, like in the Cranial Contrast Therapy Bladder 1100, the pressure within the compression bladder may be held constant, thereby providing a steady compression on the therapy site, or may be varied dynamically, thereby providing a therapeutic, massage-like pulsation on the therapy site.

Figure 14D:
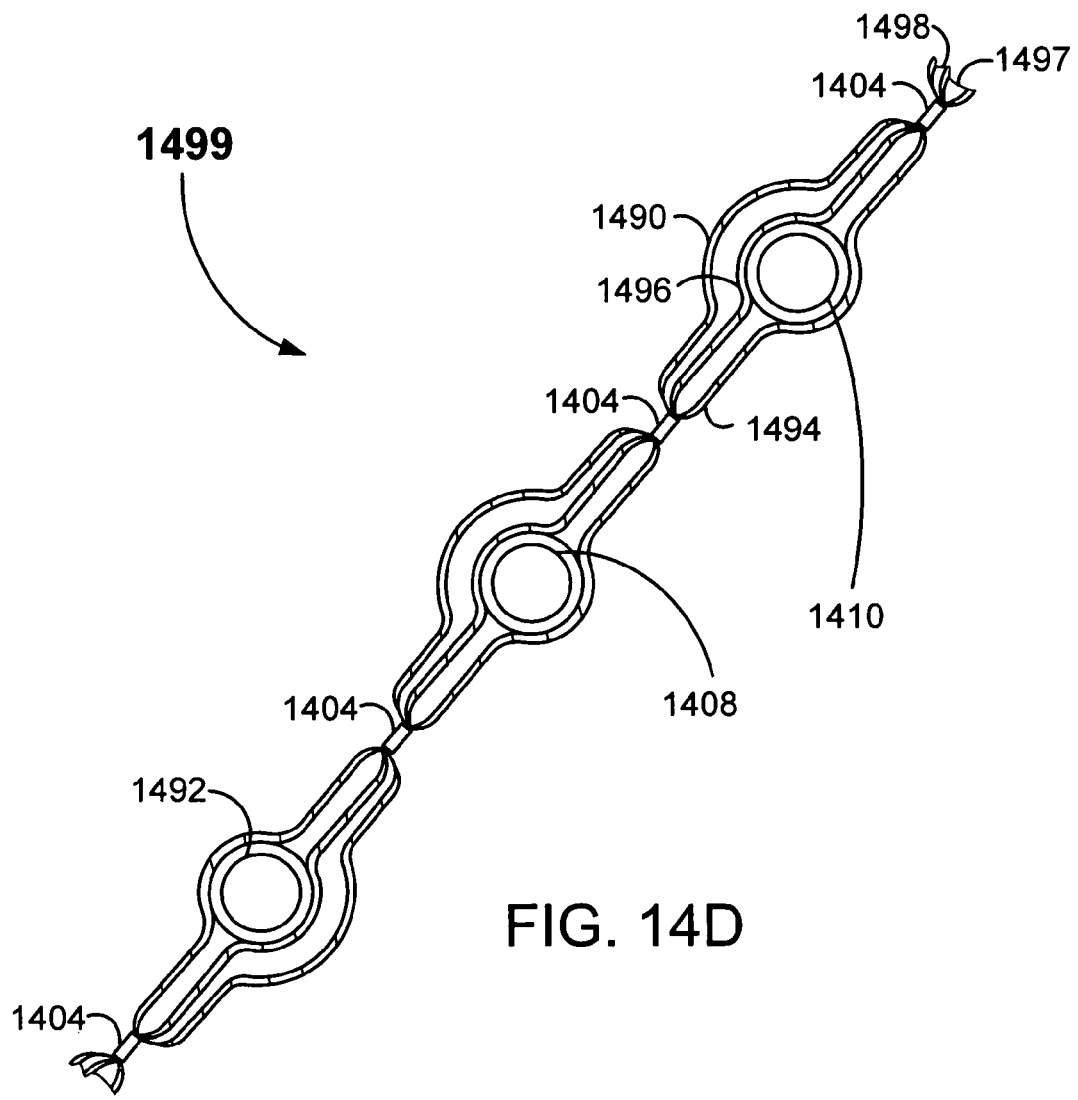
FIG. 14D is an exemplary second cross sectional illustration of the thermal bladder of the cranial wrap in accordance with an embodiment of the present invention.

FIG. 14D is an exemplary second cross sectional illustration of an Amalgamated Bladder 1499 usable in the Therapeutic Cranial Wrap 920 in accordance with an embodiment of the present invention. In some embodiment, the Amalgamated Bladder 1499 combines both a Fluid Layer 1497 and a Pneumatic Layer 1498. The Fluid Layer 1497 functions similarly equivalent to the Cranial Contrast Therapy Bladder 1100 and may provide thermal therapy to the therapy site. The Pneumatic Layer 1498 likewise functions similarly equivalent to the compression bladder and may provide compression to the therapy site. Thus, the Amalgamated Bladder 1499 may replace both the Cranial Contrast Therapy Bladder 1100 and the compression bladder in some embodiment. The Amalgamated Bladder 1499 may be placed in an envelope of mesh or other suitable material. The Fluid Layer 1497 surface of the Amalgamated Bladder 1499 may be placed against the therapy site to promote efficient thermal transfer. The Pneumatic Layer 1498 thus presses the Fluid Layer 1497 against the therapy site and provides thermal insulation for the Fluid Layer 1497, limiting thermal exchange with the external environment that does not perform a therapeutic function, and thereby increasing Fluid Layer 1497 efficiency.

In some embodiment, the Amalgamated Bladder 1499 may include a First Membrane 1490, a Second Membrane 1496 and a Third Membrane 1494 sealed around the outer perimeter. The First Membrane 1490 and Second Membrane 1496 may define the Pneumatic Layer 1498 volume for pressurized expansion. The Second Membrane 1496 and Third Membrane 1494 may define the Fluid Layer 1497 volume for therapeutic fluid flow. The First Membrane 1490, Second Membrane 1496 and Third Membrane 1494 may additionally be welded together at the Intermittent Welds 1404 to provide durability to the Amalgamated Bladder 1499 and prevent over inflation of the Fluid Layer 1497 or the Pneumatic Layer 1498. The First Membrane 1490, Second Membrane 1496 and Third Membrane 1494 may be made of the same material, or may include different materials depending upon the characteristics desired. For instance, it may be desired that the First Membrane 1490 be more elastic than the Second Membrane 1496 or Third Membrane 1494, thereby allowing for greater expansion of the Pneumatic Layer 1498.

The fluid layer connecter Bladder Inlet 1408 and Bladder Outlet 1410 may be seen inserting the Amalgamated Bladder 1499 between the Second Membrane 1496 and Third Membrane 1494, thereby providing therapy fluid to the Fluid Layer 1497. Likewise, the Pneumatic Connector 1492 may insert between the Second Membrane 1496 and First Membrane 1490, thereby providing pressure control to the Pneumatic Layer 1498.

Additionally, the Amalgamated Bladder 1499 may vary in shape and size in order to accommodate particular therapeutic desires or Therapeutic Cranial Wrap 920 configurations.

In some embodiments, the Amalgamated Bladder 1499 may be constructed with disposable materials. For example, Amalgamated Bladder 1499 configured for a single use may be constructed from disposable materials, which are usually less expensive than reusable materials. The disposable Amalgamated Bladder 1499 may be particularly useful in emergency, trauma, or post surgery situations. Amalgamated Bladder 1499 may alternatively be configured to be washable, such as by a laundry machine, and therefore may be sanitarily reused.

VII. Method of Administering Contrast of Thermal Therapy

FIG. 15 shows, generally at 1500, a method of administering contrast therapy to a therapy recipient. Method 1500 includes, at 1502, providing a volume of a relatively hot fluid. As explained above, a fluid may be received by a hot reservoir, where it may be heated by a heater. The relatively hot fluid may be virtually any temperature, with temperatures of approximately 100 to 105 degrees Fahrenheit being suitable for many applications. The method further includes, at 1504, providing a volume of a relatively cold fluid. Fluid may be received by a cold reservoir, where it may be cooled. In some embodiments, ice slurry is used to cool fluid passing through the cold reservoir, and in some embodiments a cooler is used. The cold fluid may be virtually any temperature (cooler than the hot fluid), with temperatures of approximately 32 to 45 degrees Fahrenheit being suitable for many applications.

At 1506, the method includes selecting relative amounts of the hot and cold fluids to mix as a therapy fluid with a desired initial therapy temperature. A mixture of hot and cold fluids with a specific ratio may be selected with a mixing valve, or similar mechanism, that is configured to receive the hot and cold fluids, and pass the mixture of the hot and cold fluids as a therapy fluid. The ratio of hot to cold fluid in the therapy fluid may range from 100% hot fluid to 100% cold fluid, as well as any intermediate ratio. The temperature of the therapy fluid corresponds to the ratio of hot and cold fluids mixed, with greater percentages of hot fluid resulting in higher temperatures, and greater percentages of cold fluid resulting in cooler temperatures. The therapy fluid's maximum temperature is approximately the temperature of the hot fluid, and is achieved by selecting a ratio of all hot fluid and no cold fluid. Similarly, the therapy fluid's minimum temperature is approximately the temperature of the cold fluid, and is achieved by selecting a ratio of all cold fluid and no hot fluid.

As shown at 1508, the method further includes circulating the therapy fluid with the initial therapy temperature through a Therapy Pad 22, which includes the Hood Shaped Therapy Pad 922 of the present invention. The therapy fluid may be circulated in a pulsing stream, so as to impart a vibration that is useful in providing a therapeutic massage. Of course, the flow may instead be smooth. At 1510, the method includes applying the Therapy Pad 22, here a Hood Shaped Therapy Pad 922, to the therapy recipient. This may be performed by donning the Therapeutic Cranial Wrap 920. The Therapeutic Cranial Wrap 920 additionally supplies neck support, and therapy site compression, which may aid in the overall therapy. The temperature of the therapy fluid may be translated through the Therapy Pad 22, here a Hood Shaped Therapy Pad 922, to the therapy recipient. For example, if the initial temperature of the therapy fluid is relatively hot, for instance 105 degrees Fahrenheit, the Hood Shaped Therapy Pad 922 may be used to heat a therapy site on the therapy recipient. Similarly, a therapy fluid with a relatively cold therapy temperature, such as 40 degrees Fahrenheit, may be used to cool a therapy site.

The method further includes, at 1510, returning the therapy fluid to at least one of the volume of hot fluid and the volume of cold fluid. Returning the therapy fluid to either or both of the volumes of hot and cold fluids allows the therapy fluid to be recycled. The returned therapy fluid may then be heated and/or cooled, and eventually may be recirculated to the Therapy Pad 22, here the Hood Shaped Therapy Pad 922. In this manner, a limited volume of fluid in a system may be used to provide an ongoing therapy. The fluid may be repeatedly heated and/or cooled, and thus the character of the treatment may be continually changed.

As shown at 1512, the method may also include selecting relative amounts of the hot and cold fluids to mix as a therapy fluid with a desired contrast therapy temperature different than the initial therapy temperature. By changing the relative amounts of hot and cold fluids, the resulting temperature of the therapy fluid may be changed, which changes the therapy received by the therapy recipient. It is within the scope of the invention to make such temperature changes quickly, such as in under a minute, which may result in an average temperature change greater than 1 degree Fahrenheit per second. At 1514, the method may further include circulating the therapy fluid with the contrast therapy temperature through the Therapy Pad 22, here the Hood Shaped Therapy Pad 922. Circulating the therapy fluid with the contrast therapy temperature allows the therapy recipient to experience a cold treatment immediately after a hot treatment or a hot treatment immediately after a cold treatment. It should be understood that the period of change between respective treatments is ideally very small, such as under one minute. This process may be repeated one or more times, and each time the relative amounts of hot and cold fluids may be selected to result in a desired therapy temperature.

The present invention can also be practiced with other techniques for providing thermal or contrast therapy to a therapy recipient. For example, it is possible, using the Therapeutic Cranial Wrap 920 of the instant invention, to be configured to incorporate massage pads for massage therapy at the therapy site as well.

Additionally, it should be noted that due to the particular vascular activity of migraines and headaches, contrast therapy may be undesired and instead a constant temperature may be preferred. For example, since migraine pain is due to vasodilatation, a cold therapy may be beneficial for the migraine sufferer to dull pain and cause the capillaries to constrict, thereby eliminating the pain source. Likewise, since in traditional compression and tension headaches there is vasoconstriction, heat therapy may aid by dilating the capillaries and relieving constriction.

In sum, the present invention provides a cranial wrap which integrates a thermal exchange layer hood, thereby providing the ability to engage in temperature or contrast therapy on the head and neck with unmatched ease. The advantages of such a cost-effective and efficient system include ease of use, reduced pain by the wearer, shorter preparation time for contrast therapy, enhanced neck support, ease of cleaning, and ability to share the cranial wrap device among different therapy recipients in an institutional or outpatient environment.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A therapeutic cranial wrap system for a therapy recipient, the therapeutic cranial wrap system comprising:
    an active thermal exchange bladder configured to fit a cranial therapy site of the therapy recipient, wherein the active thermal exchange bladder includes at least one fluid channel for receiving a therapy fluid, and wherein the cranial therapy site includes at least one of the therapy recipient's forehead, the therapy recipient's temples, the therapy recipient's dorsal neck region, and the therapy recipient's occipital cranium region;
    a contoured shell configured to snugly fit the cranial therapy site, and further configured to provide neck support, wherein the contoured shell is coupled to the active thermal exchange bladder, and wherein the contoured shell maximizes contact between the active thermal bladder and the therapy site;
    an adjustable strapping system configured to secure the contoured shell coupled to the active thermal exchange bladder in a fitted position adjacent the cranial therapy site and compress the active thermal exchange bladder against the cranial therapy site, and wherein the adjustable strapping system maximizes contact between the active thermal bladder and the therapy site, wherein the adjustable strapping system includes at least one adjustable cranium circumventing strap, and wherein the adjustable strapping system enables the therapeutic cranial wrap system to be used by a second therapy recipient of different head size and morphology;
    at least one cushion layer, adapted to provide comfort and adapted to aid in securing the therapeutic cranial wrap system in the fitted position adjacent the cranial therapy site and
    a thermal contrast therapy system configured to provide the therapy fluid to the active thermal exchange bladder, wherein the thermal contrast therapy system includes a hot reservoir for holding a warmer fluid, a cold reservoir for holding a colder fluid, a mixing valve for receiving a selected ratio of the warmer and colder fluids from the warm and cold reservoirs and operable to deliver the therapy fluid with a therapy temperature determined by the selected ratio, and a fluid pump for delivering the therapy fluid to the thermal exchange bladder, and wherein the thermal contrast therapy system couples to the active thermal exchange bladder.

2. The therapeutic cranial wrap system of claim 1, wherein the contoured shell includes varying levels of neck support.

3. A therapeutic cranial wrap system in combination with a thermal contrast therapy system for a therapy recipient, the therapeutic cranial wrap comprising:
    an active thermal exchange bladder configured to fit a cranial therapy site of the therapy recipient, wherein the active thermal exchange bladder is coupled to the thermal contrast therapy system, and wherein the active thermal exchange bladder includes at least one fluid channel for receiving a therapy fluid, and wherein the cranial therapy site includes at least one of the therapy recipient's forehead, the therapy recipient's temples, the therapy recipient's dorsal neck region, and the therapy recipient's occipital cranium region;
    an active compression bladder configured to fit the cranial therapy site for providing compression to the cranial therapy site, wherein the active compression bladder is coupled to a pump for providing fluid under pressure;
    a contoured shell configured to snugly fit the cranial therapy site, and further configured to provide neck support, wherein the contoured shell is coupled to the active thermal exchange bladder and the active compression bladder, and wherein the contoured shell maximizes contact between the active thermal bladder and the therapy site;
    at least one cushion layer, adapted to provide comfort and adapted to aid in securing the therapeutic cranial wrap system in the fitted position adjacent the cranial therapy site and
    an adjustable strapping system configured to secure the contoured shell coupled to the active thermal exchange bladder in a fitted position adjacent the cranial therapy site and compress the active thermal exchange bladder against the cranial therapy site, and wherein the adjustable strapping system maximizes contact between the active thermal bladder and the therapy site, wherein the adjustable strapping system includes at least one adjustable cranium circumventing strap, and wherein the adjustable strapping system enables the therapeutic cranial wrap system to be used by a second therapy recipient of different head size and morphology.

4. The therapeutic cranial wrap system of claim 3, wherein the thermal contrast therapy system includes a warmer reservoir for holding a warmer fluid, a colder reservoir for holding a colder fluid, a mixing valve for receiving a selected ratio of the warmer and colder fluids from the warmer and colder reservoirs and operable to deliver a therapy fluid with a therapy temperature determined by the selected ratio, and a fluid pump for delivering the therapy fluid to the thermal exchange bladder.

5. The therapeutic cranial wrap system of claim 3, further comprising a thermal bladder envelope that receives the thermal exchange bladder and a compression bladder envelope that receives the compression bladder.

6. The therapeutic cranial wrap system of claim 3, further comprising a bladder envelop that receives both the thermal exchange bladder and the compression bladder.

7. The therapeutic cranial wrap system of claim 3, wherein the pump causes constant pressure within the compression bladder, wherein the constant pressure produces steady compression on the therapy site.

8. The therapeutic cranial wrap system of claim 3, wherein the pump causes dynamic pressure within the compression bladder, wherein the dynamic pressure produces pulsating compression on the therapy site.

9. The therapeutic cranial wrap system of claim 3, wherein the shell includes varying levels of neck support.

10. A therapeutic cranial wrap system in combination with a thermal contrast therapy system for a therapy recipient, the therapeutic cranial wrap comprising:
    an active thermal exchange and compression bladder configured to fit a cranial therapy site of the therapy recipient, wherein the active thermal exchange and compression bladder is coupled to the thermal contrast therapy system, and wherein the active thermal exchange and compression bladder includes at least one fluid channel for receiving a therapy fluid, and wherein the cranial therapy site includes at least one of the therapy recipient's forehead, the therapy recipient's temples, the therapy recipient's dorsal neck region, and the therapy recipient's occipital cranium region;
    a contoured shell configured to snugly fit the cranial therapy site, and further configured to provide neck support, wherein the contoured shell is coupled to the active thermal exchange and compression bladder, and wherein the contoured shell maximizes contact between the active thermal bladder and the therapy site;

at least one cushion layer, adapted to provide comfort and adapted to aid in securing the therapeutic cranial wrap system in the fitted position adjacent the cranial therapy site and an adjustable strapping system configured to secure the contoured shell coupled to the active thermal exchange and compression bladder in a fitted position adjacent the cranial therapy site and compress the active thermal exchange and compression bladder against the cranial therapy site, and wherein the adjustable strapping system maximizes contact between the active thermal bladder and the therapy site, wherein the adjustable strapping system includes at least one adjustable cranium circumventing strap, and wherein the adjustable strapping system enables the therapeutic cranial wrap system to be used by a second therapy recipient of different head size and morphology.

11. The therapeutic cranial wrap system of claim 10, wherein the thermal contrast therapy system includes a warmer reservoir for holding a warmer fluid, a colder reservoir for holding a colder fluid, a mixing valve for receiving a selected ratio of the warmer and colder fluids from the warmer and colder reservoirs and operable to deliver a therapy fluid with a therapy temperature determined by the selected ratio, and a fluid pump for delivering the therapy fluid to the thermal exchange bladder.

12. The therapeutic cranial wrap system of claim 10, further comprising a thermal exchange and compression bladder envelope including a first face and an opposing second face, the faces converging at a perimeter of the thermal exchange and compression bladder envelope and collectively defining a volume adapted to receive the thermal exchange and compression bladder.

13. The therapeutic cranial wrap system of claim 11, wherein the thermal exchange and compression bladder provides compression on the therapy site, wherein the compression is generated by pressure within the thermal exchange and compression bladder, and wherein the pressure is regulated by the pump of the contrast therapy system.

14. The therapeutic cranial wrap system of claim 13, wherein the pump causes constant pressure within the thermal exchange and compression bladder, wherein the constant pressure produces steady compression on the therapy site.

15. The therapeutic cranial wrap system of claim 13, wherein the pump causes dynamic pressure within the thermal exchange and compression bladder, wherein the dynamic pressure produces pulsating compression on the therapy site.

16. The therapeutic cranial wrap system of claim 10, wherein the shell includes varying levels of neck support.

17. The therapeutic cranial wrap system of claim 10, wherein the active thermal exchange and compression bladder is an active amalgamated bladder, wherein the amalgamated bladder includes a thermal exchange capability and a compressive capability.

18. The therapeutic cranial wrap system of claim 17, further comprising a pump, wherein the compression capability is generated by pressure within the amalgamated bladder, and wherein the pressure is regulated by the pump.

19. The therapeutic cranial wrap system of claim 17, wherein the thermal exchange capability of the amalgamated bladder and the compression capability are included within the same plane.

20. The therapeutic cranial wrap system of claim 17, wherein the thermal exchange capability of the amalgamated bladder and the compression capability are included within adjacent planes.

21. A method for providing cranial thermal therapy to a therapy recipient, useful in association with a therapeutic cranial wrap system, the method comprising:

identifying a source for a cranial pain perceived by the therapy recipient;

selecting a desired therapy temperature, wherein the desired therapy temperature depends upon the source of the cranial pain;

selecting a ratio of a warmer fluid and a colder fluid, wherein the ratio depends upon the desired therapy temperature;

receiving the selected ratio of the warmer fluid from a warmer fluid reservoir and the colder fluid from a colder fluid reservoir;

mixing the selected ratio of the warmer fluid and the colder fluid to generate a therapy fluid, wherein the therapy fluid has the desired therapy temperature; and circulating the therapy fluid through at least one channel of an active thermal exchange bladder of the therapeutic cranial wrap system, wherein the active thermal exchange bladder is configured to fit a cranial therapy site of the therapy recipient; and returning the initial therapy fluid to at least one of the warmer fluid reservoir and the colder fluid reservoir.

22. The method of claim 21, wherein the source of the cranial pain includes at least one of migraine, tension headache, compression headache, and trauma.

23. The method of claim 22, wherein the desired therapy temperature is relatively cold when the source of the cranial pain is the migraine.

24. The method of claim 22, wherein the desired therapy temperature is relatively hot when the source of the cranial pain is the tension headache or the compression headache.

25. The method of claim 22, wherein the desired therapy temperature includes a contrast therapy when the source of the cranial pain is trauma.

* * * * *